(12) United States Patent
Yao

(10) Patent No.: US 10,413,390 B2
(45) Date of Patent: Sep. 17, 2019

(54) OMNIDIRECTIONAL SCIENTIFIC TOOTHBRUSH

(71) Applicant: Qing Yao, Sichuan (CN)

(72) Inventor: Qing Yao, Sichuan (CN)

(73) Assignee: Qing Yao, Chengdu, Sichuan (CN)

( * ) Notice: Subject to any disclaimer, the term of this patent is extended or adjusted under 35 U.S.C. 154(b) by 0 days.

(21) Appl. No.: 15/771,457

(22) PCT Filed: Sep. 22, 2016

(86) PCT No.: PCT/CN2016/099670
§ 371 (c)(1),
(2) Date: Apr. 27, 2018

(87) PCT Pub. No.: WO2017/071434
PCT Pub. Date: May 4, 2017

(65) Prior Publication Data
US 2018/0311023 A1    Nov. 1, 2018

(30) Foreign Application Priority Data

Oct. 30, 2015 (CN) .......................... 2015 1 0732201

(51) Int. Cl.
*A61C 17/22* (2006.01)
*A61C 17/26* (2006.01)
(Continued)

(52) U.S. Cl.
CPC ............ *A61C 17/228* (2013.01); *A46B 9/045* (2013.01); *A46B 13/04* (2013.01); *A61C 17/26* (2013.01);
(Continued)

(58) Field of Classification Search
CPC ....... A61C 17/228; A61C 17/26; A61C 17/28; A46B 9/045; A46B 13/04
See application file for complete search history.

(56) References Cited

U.S. PATENT DOCUMENTS

| 3,440,680 A | 4/1969 | Werding |
| 4,538,315 A | 9/1985 | Barth |

(Continued)

FOREIGN PATENT DOCUMENTS

| CN | 201067445 | 6/2008 |
| CN | 201356672 | 12/2009 |

(Continued)

OTHER PUBLICATIONS

International Search Report for PCT/CN2016/099670 dated Nov. 22, 2016, 5 pages.

(Continued)

*Primary Examiner* — Shay Karls
(74) *Attorney, Agent, or Firm* — Dority & Manning, P.A.

(57) ABSTRACT

An omnidirectional scientific toothbrush includes a brush handle and a brush head having a U-shaped structure. A central gearset, and tooth outer side brush rollers and tooth inner side brush rollers, both of which are respectively arranged in an upper row and a lower row according to tooth layout, and a tooth end surface brush roller driven by the central gearset are installed in an inner cavity of the brush head. The tooth end surface brush roller is located in a space defined by the tooth outer side brush rollers and the tooth inner side brush rollers. The rotating action of the tooth end surface brush roller allows the tooth end surface brush roller to simultaneously brush occlusal surfaces of upper and lower rows of teeth. Thus the cleaning operation of all of the teeth in the mouth may just be finished at one time automatically.

16 Claims, 22 Drawing Sheets

(51) Int. Cl.
    *A61C 17/28*    (2006.01)
    *A46B 9/04*     (2006.01)
    *A46B 13/04*    (2006.01)
(52) U.S. Cl.
    CPC ...... *A61C 17/28* (2013.01); *A46B 2200/1066* (2013.01)

(56) References Cited

U.S. PATENT DOCUMENTS

| | | | | |
|---|---|---|---|---|
| 5,177,827 | A * | 1/1993 | Ellison | A61C 17/228 |
| | | | | 15/22.1 |
| 5,337,435 | A | 8/1994 | Krasner et al. | |
| 6,402,410 | B1 * | 6/2002 | Hall | A61C 17/36 |
| | | | | 401/146 |
| 8,668,397 | B2 * | 3/2014 | Barkhordar | A46B 11/0006 |
| | | | | 15/22.1 |

FOREIGN PATENT DOCUMENTS

| | | |
|---|---|---|
| CN | 102727320 | 10/2012 |
| CN | 103750913 | 4/2014 |
| CN | 104783916 | 7/2015 |
| CN | 204683824 | 10/2015 |
| CN | 105266915 | 1/2016 |
| CN | 205073060 | 3/2016 |
| JP | 2008029659 | 2/2008 |
| JP | 2009195575 | 9/2009 |
| KR | 20110015097 | 2/2011 |
| WO | WO2004087003 | 10/2004 |
| WO | WO2009048287 | 4/2009 |

OTHER PUBLICATIONS

European Search Report for PCT/CN2016/099670 dated Jun. 12, 2019, 6 pages.

* cited by examiner

OMNIDIRECTIONAL SCIENTIFIC TOOTHBRUSH

CROSS REFERENCE TO RELATED APPLICATIONS

This application is the U.S, National Stage entry of International Application Number PCT/ICN2016/099670, titled "OMNIDIRECTIONAL SCIENTIFIC TOOTHBRUSH", filed on Sep. 22, 2016, which claims priority to Chinese patent application No. 201510732201.5, titled "OMNIDIRECTIONAL SCIENTIFIC TOOTHBRUSH", filed with the Chinese Intellectual Property Office on Oct. 30, 2015, the entire disclosures of which are incorporated herein by reference.

FIELD

The present application relates to a toothbrush, and particularly relates to an omnidirectional scientific toothbrush.

BACKGROUND

One of the basic behaviors for guaranteeing a healthy life is tooth cleaning. In daily life, people generally use a toothbrush to clean teeth. Therefore, the toothbrush is an indispensable personal cleaning tool in people's daily life. The toothbrush is used together with a toothpaste to brush dirt on the surface of the teeth so as to clean the teeth.

At present, there are mainly two types of common toothbrushes in the market: the manual toothbrush and the electric toothbrush.

The common manual toothbrush is composed of toothbrush bristles and a toothbrush handle, and the toothbrush bristles are simply fixedly secured to one end of the toothbrush handle. Though this kind of manual toothbrush has a simple structure and is convenient, practical and cost-efficient, its disadvantages are obvious and are mainly presented in the following aspects. The contact area of the bristles with the teeth is small due to a small area of the bristles, resulting in a low cleaning efficiency and cleanliness of the tooth brushing, and the toothbrush imposes a high requirement on the manual operation of the user. If the user's brushing action is improper, it is very likely that corner areas of the teeth and gaps between the teeth are not brushed during the tooth brushing, and even the part brushed may not be brushed clean thoroughly, and in addition, it is also apt to damage the gums.

The electric toothbrushes in the market take the manual toothbrushes as prototypes, and are generally equipped with a battery, a micro-motor and a transmission mechanism, and some electric toothbrushes are additionally provided with uncertain acoustic wave technology. Since the bristles of the electric toothbrush are self-rotated or moved up and down, the user is simply required to slowly move the toothbrush handle along the direction of the teeth. Though the electric toothbrushes are superior to the manual toothbrushes, these electric toothbrushes cannot sufficiently guarantee the properness of tooth brushing action and the completeness of the tooth brushing. In addition, most of the electric toothbrushes in the market have a low cost performance and a poor practicality, and therefore cannot be widely promoted in the market.

The common issues of the above two types of toothbrushes are that the brush heads of both the toothbrushes are always small, and the shapes of the brush heads of the toothbrushes cannot ensure that they can brush everywhere of the teeth either, such as a root of a wisdom tooth and gaps between the teeth. Therefore, the user needs to manually move the toothbrush frequently to position the toothbrush so as to perform the tooth brushing. Moreover, various steps of toothpaste feeding, brushing, and washing in the tooth brushing process cannot be automatically performed, resulting in waste time and energy of tooth brushing, and the cleanliness of the teeth after the brushing cannot be guaranteed.

When brushing teeth daily, most people know that the proper and scientific tooth brushing direction is to brush the teeth vertically from the root of teeth to the cusp of teeth with a brush head of a toothbrush. However, for various considerations such as cleaning philosophy, tooth brushing habits, time stress, etc., most toothbrush users are unable or unwilling to spend too much energy or time for every time of tooth brushing to perform strictly according to the requirements of the proper and scientific tooth brushing direction, and this proper and scientific tooth brushing action cannot be performed naturally or properly either in terms of a human body structure and human body mechanics. Therefore, many people brush teeth randomly in daily life, and especially are apt to ignore the cleaning of occlusal surfaces of the teeth when brushing teeth, so that the oral cavity cleaning results obtained by tooth brushing is unsatisfactory, and the improper brushing action may even damage the gums, cause more oral diseases and impair the health of body. In particular, since the occlusal surfaces of the teeth are rough, more and more food debris are apt to be accumulated on the rough occlusal surfaces of the teeth, which greatly increases the chance of occurrence of dental caries, and ultimately impairs health of human body.

SUMMARY

A technical issue to be addressed by the present application is: to provide a new omnidirectional scientific toothbrush which confirms to human engineering and meets the requirements of a scientific tooth brushing method, and effectively improves tooth brushing efficiency of toothbrush users and cleanliness of the teeth brushed.

The technical issue to be addressed by the present application is addressed by the following technical solutions: an omnidirectional scientific toothbrush includes a brush handle and a brush head. The brush head has a U-shaped structure, and a central gearset, and tooth outer side brush rollers, tooth inner side brush rollers and a tooth end surface brush roller which are driven by the central gearset are installed in an inner cavity of the brush head, the tooth outer side brush roller and the tooth inner side brush roller are respectively arranged in an upper row and a lower row which are opposite according to tooth layout in an oral cavity of a human body. The tooth end surface brush roller is located in a space defined by the tooth outer side brush rollers and the tooth inner side brush rollers. A power output mechanism driven by a micro motor is arranged in the brush handle, the power output mechanism drives the central gearset to move, to allow the tooth outer side brush roller and the tooth inner side brush roller located at two sides of the same tooth to rotate in opposite directions and to have rotating directions which are both from a root of the tooth to an cud of the tooth. The rotating action of the tooth end surface brush roller allows the tooth end surface brush roller to simultaneously brush occlusal surfaces of upper and lower rows of teeth in the oral cavity.

Preferably, the central gearset includes a primary transmission gear, a lower secondary transmission gear and an upper secondary transmission gear, the tooth outer side brush rollers and the tooth inner side brush rollers are fixedly connected to the side brush roller gears respectively, the tooth end surface brush roller is fixedly connected to the end surface brush roller gear. The end surface brush roller gear is engaged with the primary transmission gear to transmit power, and the primary transmission gear is engaged with the lower secondary transmission gear to transmit power, and each of the primary transmission gear, the lower secondary transmission gear and the upper secondary transmission gear is engaged with a separate side brush roller gear to transmit power.

Preferably, the power output mechanism of the brush handle includes a power output gear, a brush handle transmission gear, a rotating direction output transmission gear and a motor power output gear. An output shaft of the micro motor is fixedly connected to the motor power output gear, and the rotating direction output transmission gear is formed by a bevel gear and a spur gear connected coaxially. The motor power output gear is a bevel gear and is engaged with a bevel gear of the rotating direction output transmission gear to transmit power. The brush handle transmission gear is engaged with the power output gear and the spur gear of the rotating direction output transmission gear respectively. The power output gear is engaged with the end surface brush roller gear and the upper secondary transmission gear respectively to transmit power. The primary transmission gear, the lower secondary transmission gear, the upper secondary transmission gear and the power output gear are respectively engaged with a separate side brush roller gear to transmit power.

Preferably, a main body part of the tooth end surface brush roller is a flexible roller, and a flexible cord is provided in the flexible roller, the flexible cord is fixedly connected to the end surface brush roller gear, and bristles are planted onto the flexible roller at each of two sides of the end surface brush roller gear.

Preferably, the central gearset includes a first transmission gear, a third transmission gear, a fourth transmission gear, a sixth transmission gear, a seventh transmission gear, an eighth transmission gear, a ninth transmission gear and a tenth transmission gear. The tooth outer side brush rollers and the tooth inner side brush rollers are fixedly connected to side brush roller gears respectively. Each of the first transmission gear, the third transmission gear, the fourth transmission gear and the sixth transmission gear is formed by coaxially connecting a spur gear and a face gear. The spur gear of the first transmission gear is engaged with the eighth transmission gear to transmit power, and the spur gear of the third transmission gear is engaged with the seventh transmission gear to transmit power, and the spur gear of the fourth transmission gear is engaged with the tenth transmission gear to transmit power, and the spur gear of the sixth transmission gear is engaged with the ninth transmission gear to transmit power. Each of the seventh transmission gear, the eighth transmission gear, the ninth transmission gear and the tenth transmission gear is engaged with a separate side brush roller gear to transmit power. Outer sides of the first transmission gear and the third transmission gear are respectively connected to the tooth end surface brush roller, or outer sides of the fourth transmission gear and the sixth transmission gear are respectively connected to the tooth end surface brush roller.

Preferably, the power output mechanism of the brush handle includes a central transmission shaft, a brush handle transmission gear, a rotating direction output transmission gear, a motor power output gear, a second transmission gear and a fifth transmission gear.

The central transmission shaft has one end fixedly connected to the brush handle transmission gear and another end fixedly connected to each of the second transmission gear and the fifth transmission gear. The first transmission gear and the sixth transmission gear are located on a same side of the central transmission shaft, and the third transmission gear and the fourth transmission gear are located on another same side of the central transmission shaft. The output shaft of the micro motor is fixedly connected to the motor power output gear. Opposite ends of the rotating direction output transmission gear are face gears respectively and the face gears are engaged with the brush handle transmission gear and the motor power output gear in different planes to transmit power. The face gears of the first transmission gear and the third transmission gear are respectively engaged with the second transmission gear to transmit power, and the face gears of the fourth transmission gear and the sixth transmission gear are respectively engaged with the fifth transmission gear to transmit power.

Preferably, the central gearset includes a first transmission gear, a third transmission gear, a fourth transmission gear, a sixth transmission gear, a seventh transmission gear, an eighth transmission gear, a ninth transmission gear and a tenth transmission gear. The tooth outer side brush rollers and the tooth inner side brush rollers are fixedly connected to side brush roller gears respectively. Each of the first transmission gear, the third transmission gear, the fourth transmission gear and the sixth transmission gear is formed by coaxially connecting a spur gear and a bevel gear, the spur gear of the first transmission gear is engaged with the eighth transmission gear to transmit power, and the spur gear of the third transmission gear is engaged with the seventh transmission gear to transmit power, and the spur gear of the fourth transmission gear is engaged with the tenth transmission gear to transmit power, and the spur gear of the sixth transmission gear is engaged with the ninth transmission gear to transmit power. Each of the seventh transmission gear, the eighth transmission gear, the ninth transmission gear and the tenth transmission gear is engaged with a separate side brush roller gear to transmit power. Outer sides of the first transmission gear and the third transmission gear are respectively connected to the tooth end surface brush roller, or outer sides of the fourth transmission gear and the sixth transmission gear are respectively connected to the tooth end surface brush roller.

Preferably, the power output mechanism of the brush handle includes a central transmission shaft, a brush handle transmission gear, a rotating direction output transmission gear, a motor power output gear, a second transmission gear and a fifth transmission gear. The central transmission shaft has one end fixedly connected to the brush handle transmission gear and another end fixedly connected to each of the second transmission gear and the fifth transmission gear. The first transmission gear and the sixth transmission gear are located on a same side of the central transmission shaft, and the third transmission gear and the fourth transmission gear are located on another same side of the central transmission shaft. The output shaft of the micro motor is fixedly connected to the motor power output gear, and opposite ends of the rotating direction output transmission gear are face gears respectively and the face gears are engaged with the brush handle transmission gear and the motor power output gear in different planes to transmit power. Each of the second transmission gear and the fifth transmission gear is a bevel gear, and the bevel gears of the first transmission gear and the third transmission gear are respectively engaged with the second transmission gear to transmit power, and the bevel gears of the fourth transmission gear and the sixth transmission gear are respectively engaged with the fifth transmission gear to transmit power.

Preferably, a main body part of the tooth end surface brush roller is a flexible roller, and a flexible cord is provided in the flexible roller, a tip end of the flexible cord is fixedly connected to a tooth end surface brush roller connector, and bristles are planted onto the flexible roller.

Preferably, the omnidirectional scientific toothbrush further includes a U-shaped base plate. An overall configuration of the U-shaped base plate is in a U shape, and a central gearset arranging groove is provided at a central part of the U-shaped base plate, and each of two branches of the U-shaped base plate is provided with an end surface brush roller positioning groove from a middle part to a tip end of the branch of the U-shaped base plate.

Preferably, the omnidirectional scientific toothbrush further includes a U-shaped brush head sleeve made of a flexible plastic material. The brush head sleeve is supported by a U-shaped base plate and surrounds an outer edge of the U-shaped base plate, and the brush head sleeve surrounds an outer side and an upper or lower side of the bristles.

Preferably, the omnidirectional scientific toothbrush further includes a water-washing liquid system. The water-washing liquid system includes a washing liquid storage bottle, a first one-way valve, a water pumping micro pump, a washing liquid delivery micro pump, a third one-way valve and a washing liquid delivery conduit. The washing liquid delivery conduit is installed in the brush head, and the washing liquid delivery conduit is provided with a base plate water outlet. The water pumping micro pump has one end in communication with the washing liquid delivery conduit and another end in communication with a clean water conduit and a waste water conduit. The clean water conduit is provided with the third one-way valve, and the waste water conduit is provided with the first one-way valve. The washing liquid delivery micro pump has one end in communication with the washing liquid storage bottle and another end in communication with the washing liquid delivery conduit.

Preferably, the omnidirectional scientific toothbrush further includes a clean water tank. A micro liquid level sensor is provided in the clean water tank, and the brush handle is provided with a program control unit, and an occlusal sensor is mounted on each of an upper surface and a lower surface of the U-shaped base plate in the brush head. The occlusal sensor and the micro liquid level sensor are respectively electrically connected to an input end of the program control unit, and each of the washing liquid delivery micro pump, the water pumping micro pump, the micro motor is electrically connected to an output end of the program control unit.

Preferably, the program control unit is configured to control the brushing process and performs four tooth brushing modes including: a strong brushing mode, a standard brushing mode, and a clean water washing mode and a brushing mode without clean water. The strong brushing mode includes performing a brushing sub-module first, and then performing a washing sub-module, and then cycling in the listed sequence till the end of the tooth brushing. The standard brushing mode includes performing the brushing sub-module first, and then performing the washing sub-module, and then finishing. The clean water washing mode includes simply performing the washing sub-module and then finishing. The brushing mode without clean water includes simply performing the brushing sub-module and then finishing. The brushing sub-module includes powering the washing liquid micro pump for a certain time, and then powering the micro motor, to drive the bristles to rotationally brush for a certain time and then finishing the brushing process. The washing sub-module includes forwardly connecting and powering the water pumping micro pump for a certain time, to deliver water to the brush head, and then powering the micro motor, to drive the bristles to rotationally brush for a certain time, and next, reversely connecting and powering the water pumping micro pump for a certain time, to pump water from the brush head.

Preferably, the omnidirectional scientific toothbrush further includes a brush roller terminal support. A U-shaped positioning opening is provided at each of four corners of the brush roller terminal support, and each of the tooth outer side brush rollers, the tooth inner side brush rollers and the tooth end surface brush roller is retained, by a brush roller retaining groove at respective tail end, to the brush roller terminal support.

Preferably, the brush handle is divided into a brush handle rotation part and a brush handle hold part, the brush handle rotation part has one end connected to the brush head and another end connected to the brush handle hold part, and the brush handle rotation part rotates within a certain range of angle with respect to the brush handle hold part.

Compared with the conventional technology, the beneficial effect of the present application is that the brush head has a U-shaped structure. When needing to brush teeth, the tooth outer side brush roller, the tooth inner side brush roller, and the tooth end surface brush roller of the brush head are in contact with the teeth simultaneously. The contact area for tooth brushing is large, which is different from the conventional brush in the current market that has a small brush head. In addition, all of the tooth outer side brush roller, the tooth inner side brush roller and the tooth end surface brush roller, driven by the micro motor, can have bristles omnidirectional brushing all of the teeth in scientific directions, that is, always from the roots of the teeth to the tips of the teeth when brushing the inner and outer vertical surfaces, and along the gaps of the teeth when scrubbing the occlusal surfaces of the teeth without requiring the user to manually control the frequent movement of the brush head of the toothbrush, thus the cleaning operation of all of the teeth in the mouth may just be finished at one time automatically, which significantly reduces the technical difficulties in brushing teeth with the scientific method, and improves the cleaning quality and washing efficiency of the tooth brushing, and significantly reduces the time cost and energy consumption in tooth brushing, and is scientific and efficient, and confirms to human engineering, and can maximally improve the comfort in tooth brushing. In addition, equipped with the complete water-washing liquid system and program control unit, the toothbrush according to the present application can achieve fully automatic tooth brushing with the work of the brushing sub-module and the washing sub-module, thereby further improving the cleaning efficiency in tooth brushing, and allowing the user experience to be more humanized, and intelligentized.

REFERENCE NUMERALS IN FIGS. 1 TO 31

Figure 1:
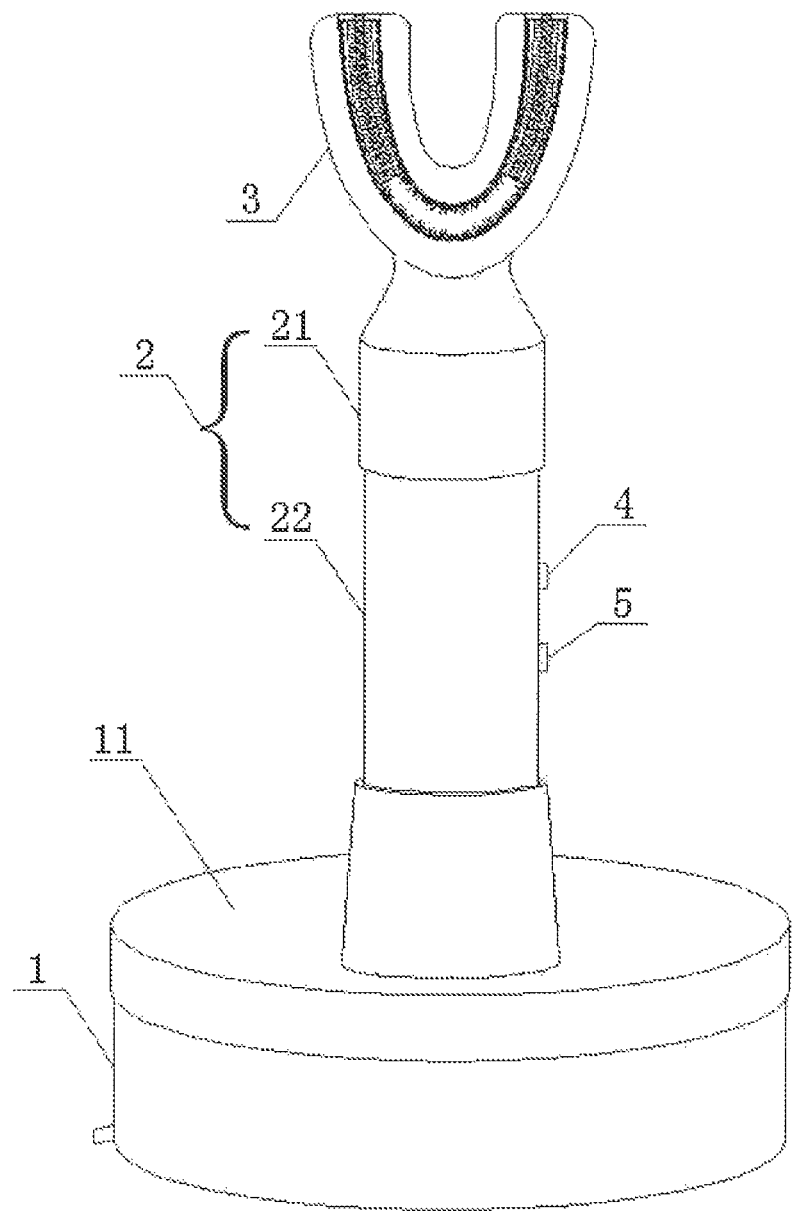
FIG. 1 is a view showing an overall configuration of an omnidirectional scientific toothbrush according to the present application.

| | |
|---|---|
| 1-base, | 2-brush handle, |
| 3-brush head, | 4-power switch, |
| 5-mode shift button, | 6-upper teeth, |
| 7-lower teeth, | 8-central transmission shaft, |
| 11-base cover plate, | |
| 21-brush handle rotation part, | 22-brush handle hold part, |
| 101-waste water outlet, | 102-waste water nozzle, |
| 103-clean water nozzle, | 104-brush handle groove, |
| 105-multi-point metal contact, | 106-down-flow hole, |
| 107-wire, | 108-micro liquid level sensor, |
| 109-clean water tank, | 110-base charging socket, |
| 111-clean water conduit, | 112-waste water conduit, |
| 201-lower water outlet, | 202-lower water inlet, |
| 203-washing liquid storage bottle, | 204-first conduit, |
| 205-first one-way valve, | 206-water pumping micro pump, |
| 207-second conduit, | 208-washing liquid delivery micro pump, |
| 209-third conduit, | 210-second one-way valve, |
| 211-power output gear, | 212-metal contact and embedded pressure switch, |
| 213-fourth conduit, | 214-brush handle transmission gear, |
| 215-wire, | 216-rotating direction output transmission gear, |
| 217-motor power output gear, | 218-micro motor, |
| 219-program control unit, | 220-fifth conduit, |
| 221-battery, | 222-multi-point metal contact strip, |
| 223-third one-way valve, | 224-brush handle charging socket, |
| 301-brush head inlet and outlet, | 302-tooth outer side brush roller, |
| 303-tooth end surface brush roller, | 304-washing liquid delivery conduit, |
| 305-end surface brush roller positioning groove, | 306-brush roller terminal support, |
| 307-tooth inner side brush roller, | 308-brush head sleeve, |
| 309-central gearset, | 310-U-shaped base plate, |
| 311-occlusal sensor, | 312-connection wire, |
| 313-brush head metal contact strip, | 314-bristles, |
| 315-flexible roller bar, | 316-side brush roller gear, |
| 317-flexible cord, | 318-end surface brush roller gear, |
| 319-primary transmission gear, | 320-lower secondary transmission gear |
| 321-central gearset support, | 322-upper secondary transmission gear, |
| 323-base plate hollow steel-wire tube, | 324-base plate water outlet hole, |
| 325-central gearset arranging groove, | 326-first transmission gear, |
| 327-second transmission gear, | 328-third transmission gear, |
| 329-fourth transmission gear, | 330-fifth transmission gear, |
| 331-sixth transmission gear, | 332-seventh transmission gear, |
| 333-eighth transmission gear, | 334-ninth transmission gear, |
| 335-tenth transmission gear, | 336-tooth end surface brush roller connector, |
| 337-gearset support housing, | |
| 3020-brush roller trailing terminal, | 3021-brush roller retaining groove. |

DETAILED DESCRIPTION OF EMBODIMENTS

In order to make the objectives, technical solutions, and advantages of the present application clearer the present application is described in detail hereinafter with reference to the drawings and embodiments. It should be understood that the embodiments described herein are only intended to explain the present application rather than limiting the present application.

First Embodiment

An omnidirectional scientific toothbrush shown in FIG. 1 is an electric toothbrush, and includes three independent parts, i.e., a base 1, a brush handle 2 and a U-shaped brush head 3. The brush handle 2 has a head connected to the U-shaped brush head 3 and a tail end inserted into the base 1.

Figure 2:
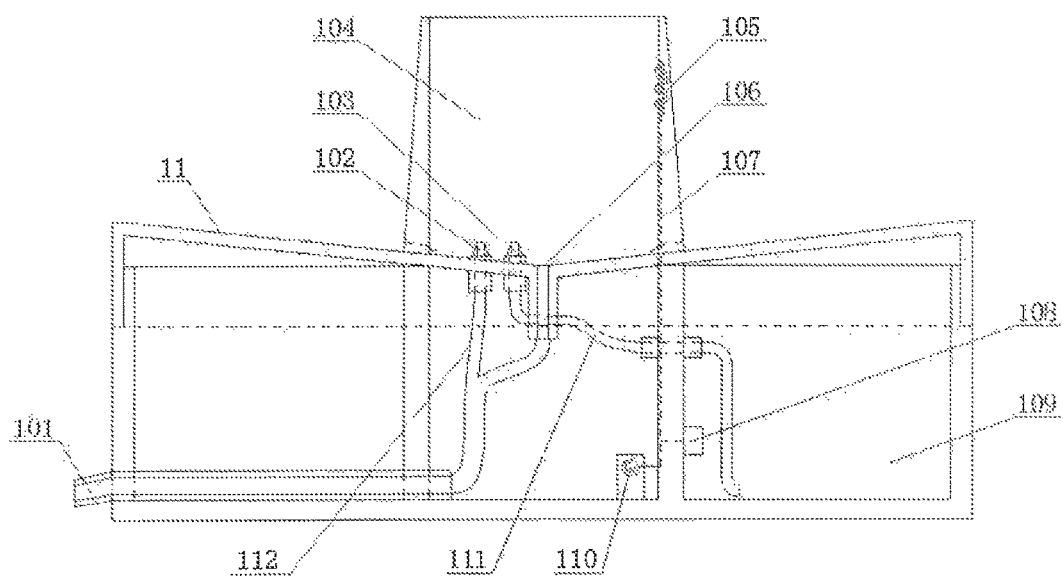
FIG. 2 is a schematic view showing the structure of a base in FIG. 1 (a first embodiment).

Specifically, as shown in FIG. 2, a main body of the base 1 is a cylindrical hollow cavity, and a base cover plate 11 is provided at the top of the base 1. The base cover plate 11 is provided with a boss, and a brush handle groove 104 is provided at a central part of the boss, and the tail end of the brush handle 2 is movably sleeved with the base 1 through the brush handle groove 104 in a plug-in manner.

Figure 4:
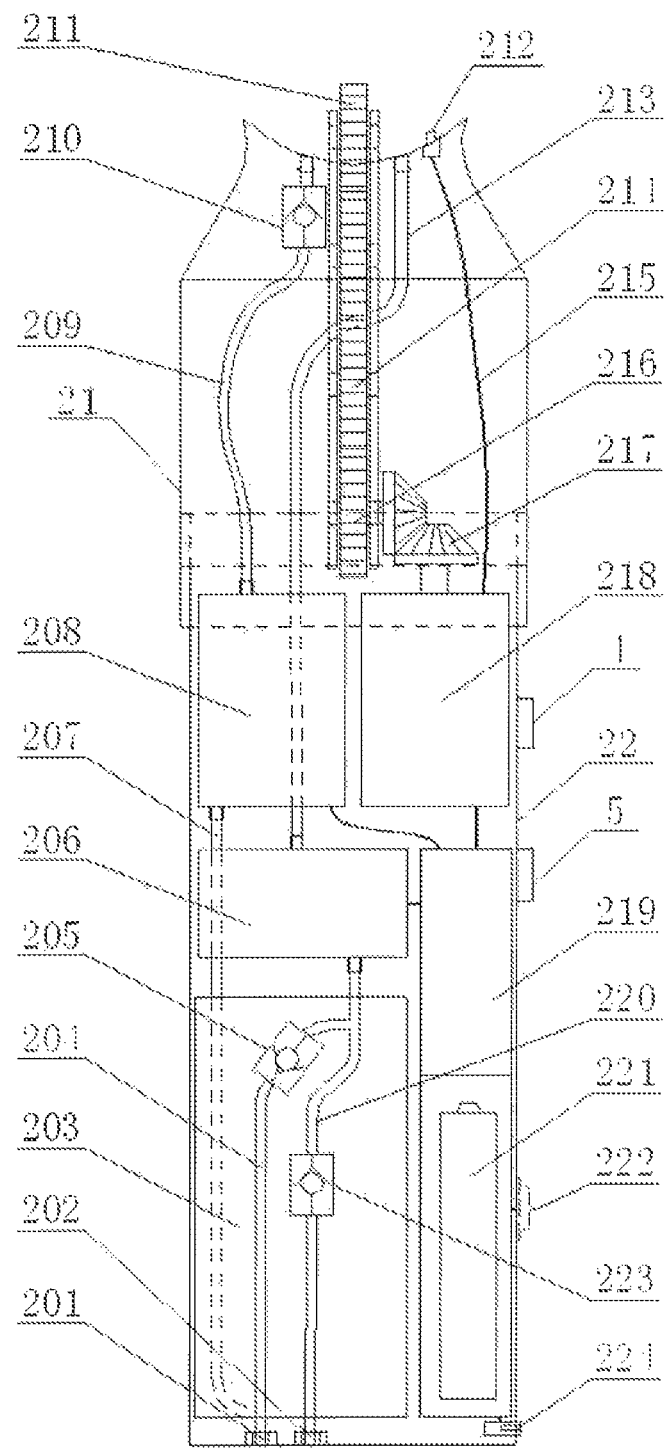
FIG. 4 is a schematic view showing the structure of a brush handle in FIG. 1 (a first embodiment).
Figure 16:
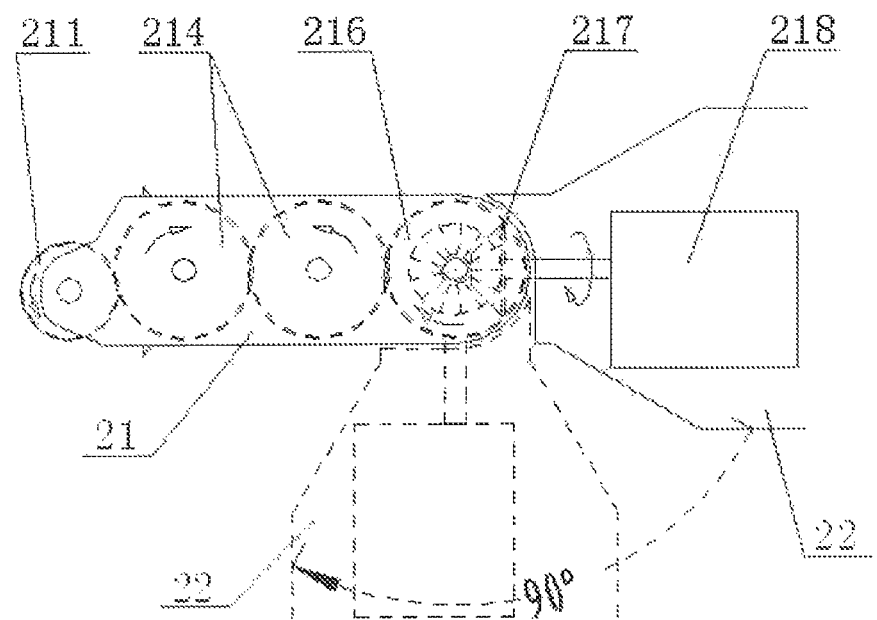
FIG. 16 is a diagram showing the principle of transmission inside the brush handle (including a schematic diagram of the rotating direction of the brush handle according to a first embodiment).

As shown in FIG. 4, the brush handle 2 is a hollow cavity, and a micro motor 218, a brush handle power output mechanism, a battery 221 and a battery cartridge thereof are provided inside the brush handle 2. A power switch 4 and a mode shift button 5 and a multi-point metal contact strip 222 are provided at a main body part of the brush handle 2. A metal contact and embedded pressure switch 212 is provided at the top of the brush handle 2. A lower water outlet 201, a lower water inlet 202 and a brush handle charging socket 224 are provided at the bottom of the brush handle 2. As shown in FIG. 16, the power output mechanism inside the brush handle 2 includes a power output gear 211, a brush handle transmission gear 214, a rotating direction output transmission gear 216 and a motor power output gear 217. An output shaft of the micro motor 218 is fixedly connected to the motor power output gear 217, and the rotating direction output transmission gear 216 is formed by coaxially connecting a bevel gear and a spur gear. The motor power output gear 217 is a bevel gear and is engaged with the bevel gear of the rotating direction output transmission gear 216 to transmit power, and the brush handle transmission gear 214 is engaged with the power output gear 211 and the spur gear of the rotating direction output transmission gear 216 respectively to transmit power.

Figure 5:
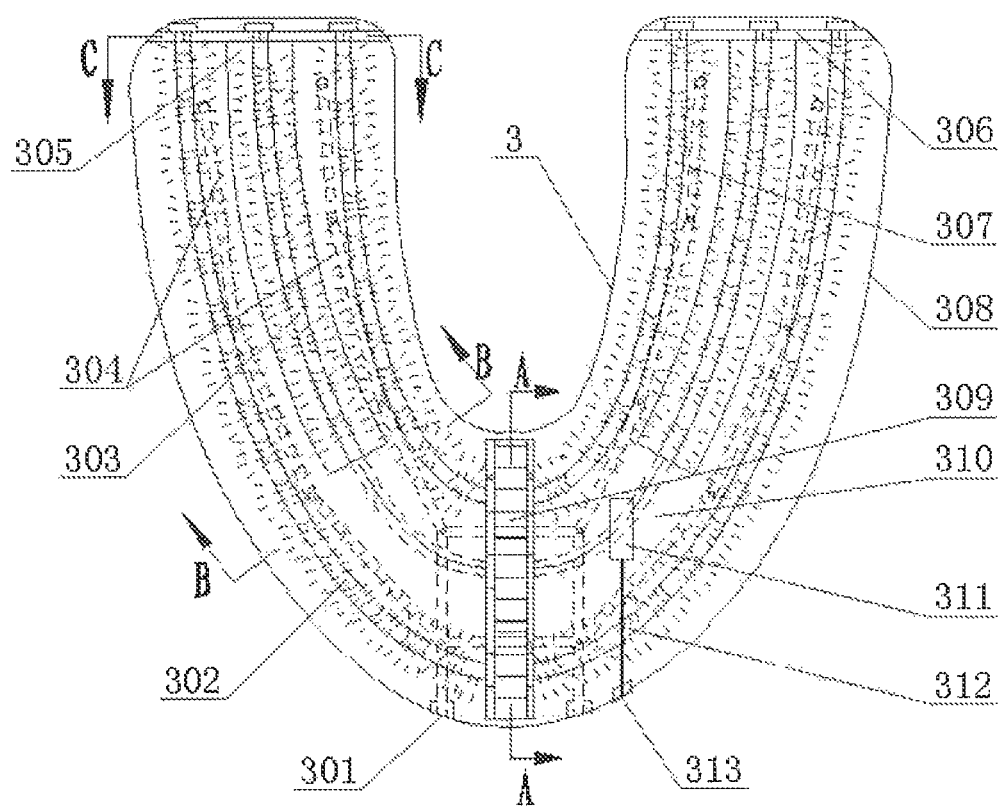
FIG. 5 is a schematic plan view of a U-shaped brush head in FIG. 1.
Figure 14:
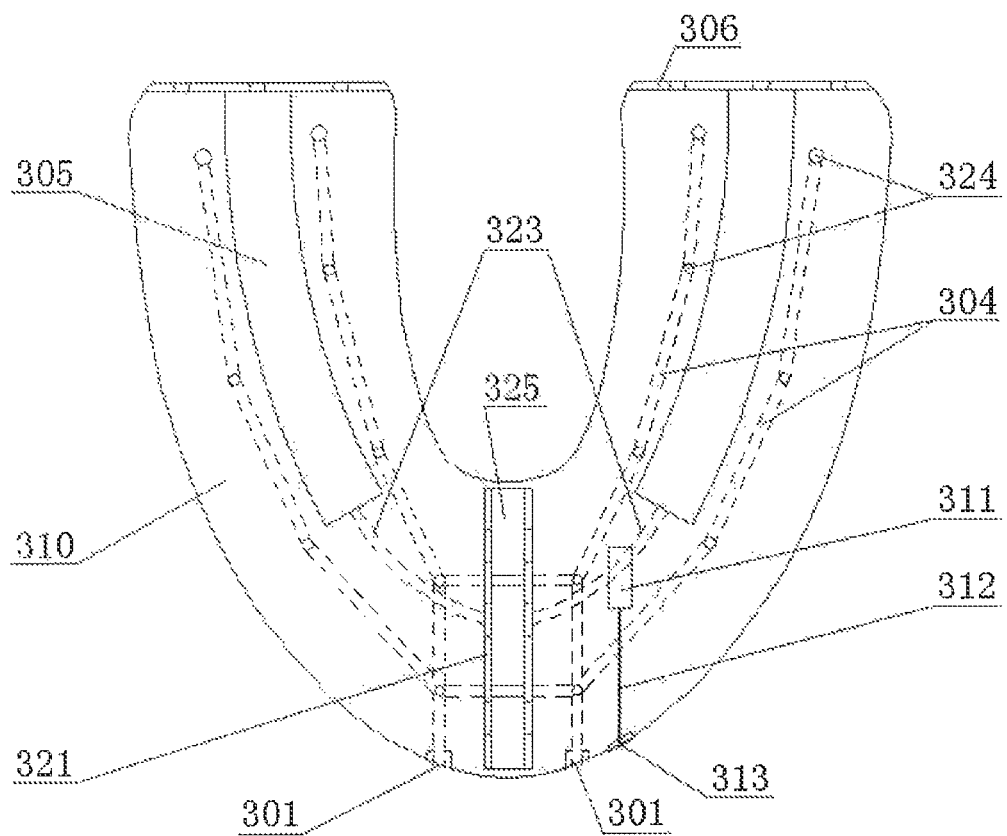
FIG. 14 is a plan view showing a configuration of a U-shaped base plate in FIG. 5.

The U-shaped brush head 3 is a core part of the entire toothbrush. As shown in FIG. 5, a brush roller terminal support 306, a rubber brush head sleeve 308, a plastic U-shaped base plate 310, a central gearset 309 and a central gearset support 321 as well as a tooth outer side brush roller 302, a tooth inner side brush roller 307 and a tooth end surface brush roller 303 which are driven by the central gearset 309 are installed in an inner cavity of the U-shaped brush head 3. The structure of the U-shaped base plate 310 is shown in FIG. 14, and has an overall U-shape. The cross section of a middle part of the U-shaped structure has the shape of a vase which is horizontally placed with two ends large and a middle portion convex or is a rectangular shape approximate to a horizontally disposed English capital letter "I". Each of tail ends of two branches of the U-shaped structure has a cross sectional shape approximate to the cross sectional shape of the middle part of the U-shaped structure and has a hollow rectangular-shaped or circular-shaped portion running through from upper side to lower side. A central gearset arranging groove 325 is provided in the central cross section of the U-shaped base plate 310 at the center to be perpendicular to a plate surface direction of the U-shaped base plate 310. In each of the two branches of the U-shaped base plate 310, an end surface brush roller positioning groove 305 is provided from a middle part to a tip end, and a base plate hollow steel-wire tube 323 and a washing liquid delivery conduit 304 are provided in a central horizontal layer of the U-shaped base plate 310, and multiple base plate water outlets 324 are provided in an upper side and a lower side of the base plate surface at portions corresponding to the washing liquid delivery conduit 304. Brush head inlet and outlet 301 and a brush head metal contact strip 313 are provided at a portion at the bottom of the U-shaped base plate 310, where the U-shaped brush head 3 is connected with the brush handle 2. An occlusal sensor 311 is provided on each of an upper surface and a lower surface of the U-shaped base plate 310a at a middle and front part thereof, and the occlusal sensor 311 is connected to the brush head metal contact strip 313 by a connection wire 312. All of the base plate water outlets 324 are in communication with the washing liquid delivery conduit 304, and the washing liquid delivery conduits 304 in the two branches of the U-shaped base plate 310 are in communication with each other and are in communication with the brush head inlet and outlet 301. The U-shaped base plate 310 functions as a support framework of the U-shaped brush head 3 and a fixing platform for the brush head components and functions to restrict and position the tooth outer side brush roller 302, the tooth inner side brush roller 307 and the tooth end surface brush roller 303.

A vertical surface of an edge of the U-shaped base plate 310 is adaptively fixed at a position of an inner wall of the brush head sleeve 308 near a central horizontal plane of the inner wall, and the U-shaped base plate 310 and the brush head sleeve 308 form vertically symmetric U-shaped grooves, with each of which having an approximate "( )" shape and an approximate "(-)" shaped cross section. In the brush head sleeve 308, the U-shaped base plate 310 is horizontally centered and is perpendicular to the inner wall of the brush head sleeve 308, and two tooth outer side brush rollers 302 and two tooth inner side brush rollers 307 are respectively disposed at joints of an upper edge and a lower edge of the U-shaped base plate 310 with the brush head sleeve 308, and are in a U-shape following the edge. A flexible cord 317 at the middle of the tooth end surface brush roller 303 is partially disposed in the base plate hollow steel-wire tube 323 along a transverse axis of the U-shaped base plate 310, and the flexible roller bars 315 at rear half parts of two ends of the tooth end surface brush roller 303 are respectively disposed in the end surface brush roller positioning grooves 305 of the two branches of the base plate. The brush roller trailing terminals 3020 of all the brush rollers are fixed to the brush roller terminal support 306 at the tail end of the U-shaped base plate 310. The central gearset 309 is fixed to the central gearset support 321, and then is placed together with the central gearset support 321 into the central gearset arranging groove 325 to be fixed. The central gearset support 321 is fixed vertically at the center of the cross section which is right at the center of the U-shaped base plate 310.

The U-shaped base plate 310 supports the brush head sleeve 308 surrounding at an outer edge of the U-shaped base plate 310. The overall shape of the brush head sleeve 308 is U-shaped, and an inner edge of a horizontal central cross section of the brush head sleeve 308 has a shape fitted with that of the outer edge of the U-shaped base plate 310, and the cross section of the brush head sleeve 308 has a shape of two semi-circles opening inwards and arranged symmetrically close to the axis. The brush head sleeve 308 is fixed to the outer edge of the U-shaped base plate 310 at a position in the central horizontal plane, and is a housing of the entire U-shaped brush head 3. The brush head sleeve 308 is made of rubber or a similar flexible plastic material, and functions to wrap and protect the U-shaped brush head 3, to define a maximum space of the U-shaped brush head 3, to fix the tooth outer side brush roller 302, the tooth inner side brush roller 307 and the tooth end surface brush roller 303 and form a relatively closed washing space, and to prevent the human body from contacting with the components of the tooth brush head, thereby achieving a good human body protective effect and a comfortable feeling.

Figure 11:
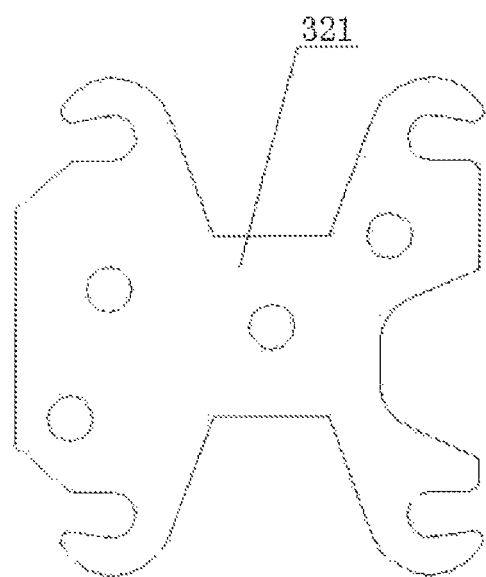
FIG. 11 is a front view of a central gearset support in FIG. 10.
Figure 12:
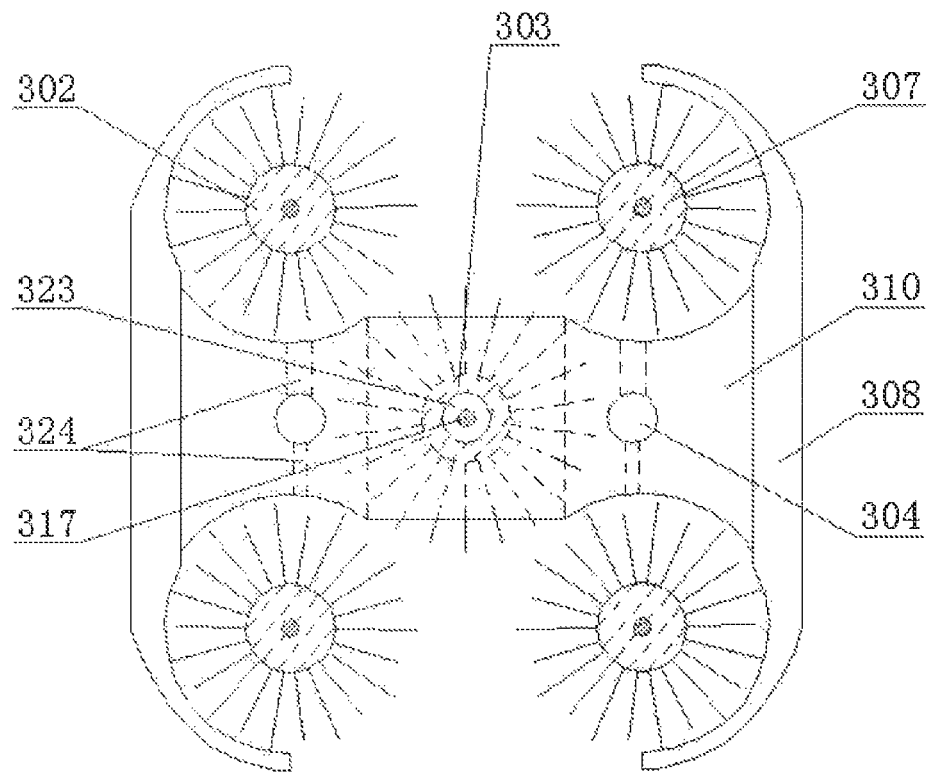
FIG. 12 is a cross-sectional view taken along a direction B-B in FIG. 5.
Figure 13:
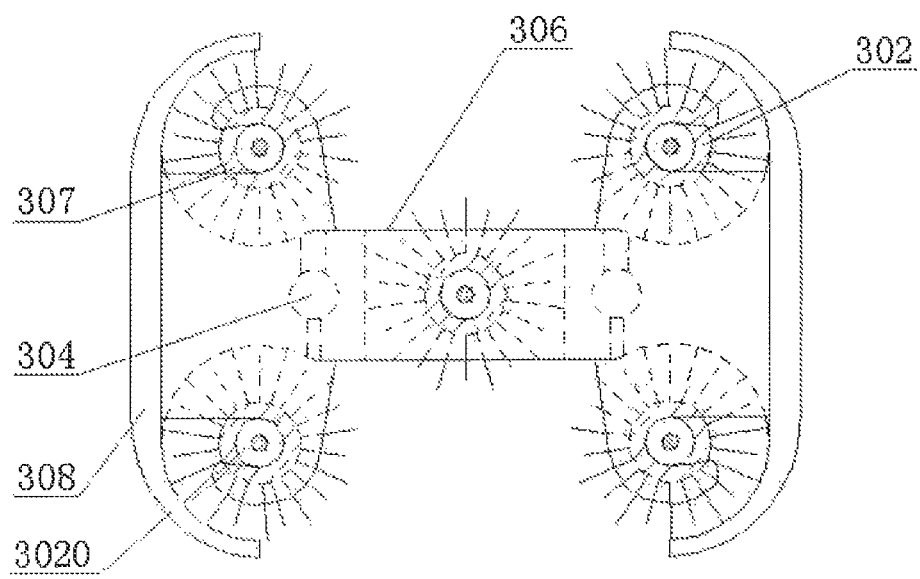
FIG. 13 is a cross-sectional view taken along a direction C-C in FIG. 5.

The central gearset 309 is supported and fixed in the U-shaped brush head 3 by the central gearset support 321, and the structure of the central gearset support 321 is as shown in FIG. 11. A U-shaped positioning opening is provided at each of four corners of the central gearset support 321, and a plurality of through-holes are provided at a central part of the central gearset support 321. The central gearset support 321 functions to fix the central gearset 309 to a central cross section of the U-shaped base plate 310, to fix and retain the tooth outer side brush roller 302, the tooth inner side brush roller 307, the tooth end surface brush roller 303 to proper tooth brushing positions, to maintain a safe distance between the gears and the teeth, and to facilitate the separation and replacement of the tooth outer side brush roller 302, the tooth inner side brush roller 307 and the tooth end surface brush roller 303.

Figure 10:
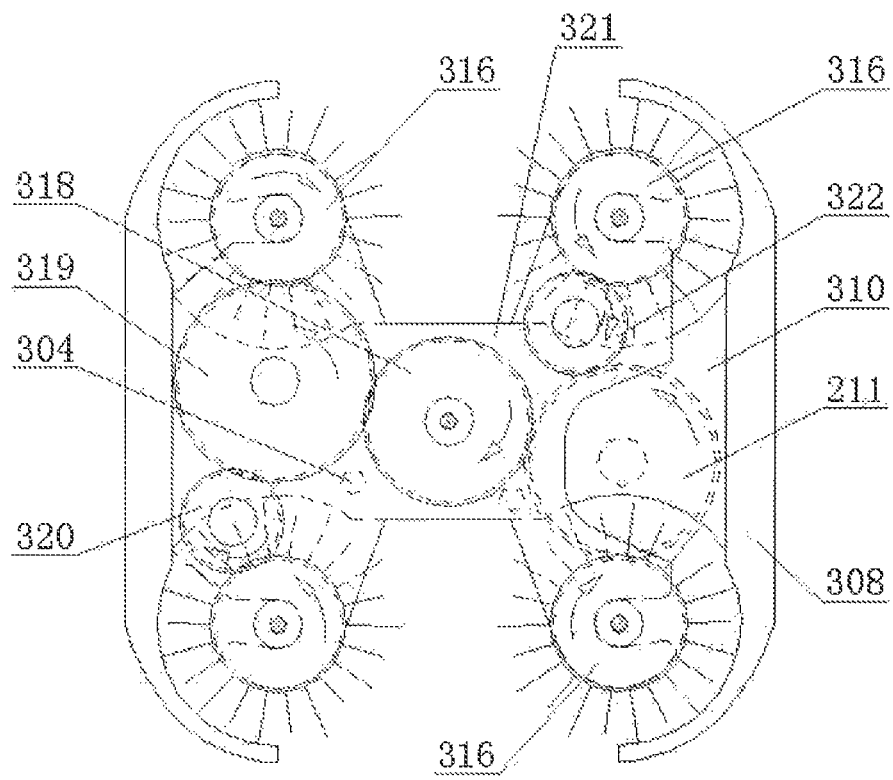
FIG. 10 is a cross-sectional view taken along a direction A-A in FIG. 5.
Figure 15:
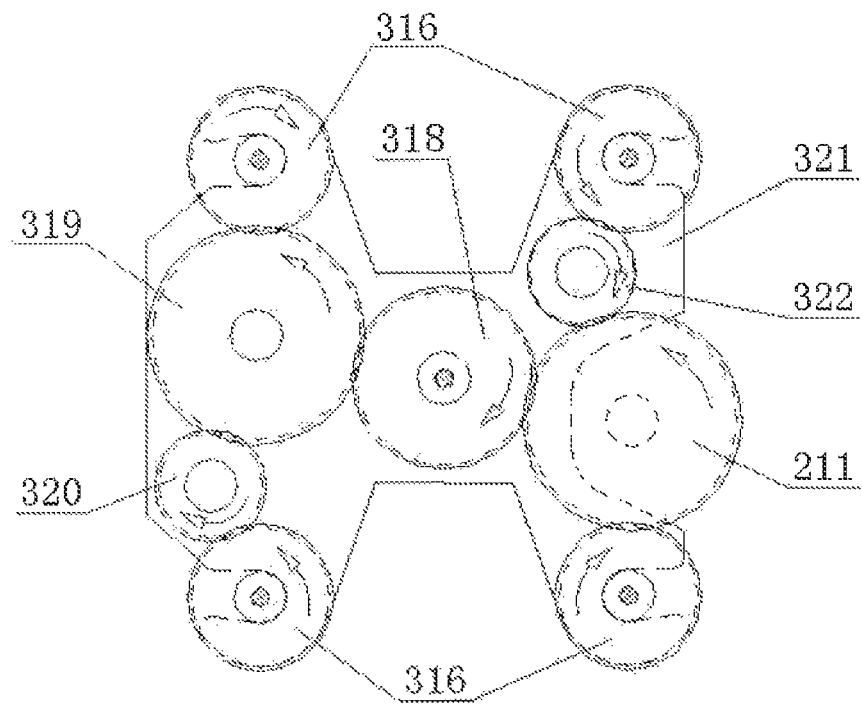
FIG. 15 is a diagram showing the principle of an engaged transmission of the central gearset in the U-shaped brush head (a first embodiment of the configuration of the central gearset).

The central gearset 309 has a configuration as shown in FIGS. 10 and 15, and is a spur gearset in the same vertical plane, which specifically includes a primary transmission gear 319, a lower secondary transmission gear 320 and an upper secondary transmission gear 322. The power output gear 211 is engaged with the end surface brush roller gear 318 and the upper secondary transmission gear 322 to transmit power. The end surface brush roller gear 318 is in turn engaged with the primary transmission gear 319 to transmit power, and the primary transmission gear 319 is further engaged with the lower secondary transmission gear 320 to transmit power. Each of the primary transmission 319, the lower secondary transmission gear 320, the upper secondary transmission gear 322, the power output gear 211 is engaged with a separate side brush roller gear 316 to transmit power.

The key points of the sizes and the position arrangement of the gears in the central gearset 309 are described as follows. The shortest distance between the two side brush roller gears 316 at an upper side or a lower side of the end surface brush roller gear 318 is mainly arranged to be adapted to the thickness of the teeth and the length of the bristles 314 at the two sides. The shortest distance between a middle point between the two side brush roller gears 316 at the upper side or the lower side of the end surface brush roller gear 318 and an outer edge of the end surface brush roller gear 318 is mainly arranged to be adapted to the height of the teeth. The sizes and relative positions of the gears directly affect the reasonableness of the above two distances and the adaptability of the brush head when entering the mouth and the quality of tooth brushing, and the minimum thickness of the U-shaped base plate 310 is determined based on the diameter of the end surface brush roller gear 318.

The tooth outer side brush roller 302 and the tooth inner side brush roller 307 are arranged symmetrically with respect to the U-shaped base plate 310 according to the arrangement of the teeth in the oral cavity of the human body, one tooth brush roller 302 and one tooth inner side brush roller 307 are arranged at the upper side and one tooth brush roller 302 and one tooth inner side brush roller 307 are arranged at the lower side. The tooth end surface brush roller 303 is located between the tooth outer side brush rollers 302 and the tooth inner side brush rollers 307. The brush roller parts of the tooth outer side brush rollers 302, the tooth inner side brush rollers 307 and the tooth end surface brush roller 303 are restrained and fixed by the U-shaped base plate 310, the brush head sleeve 308, the central gearset support 321 and the brush roller terminal support 306 into a U-shape, and wrap all of the teeth to be cleaned from the inner side, the outer side, and the upper or lower side, as shown in FIGS. 10, 12, 13, and 27. The rubber brush head sleeve 308 surrounds at the outer side and the upper or lower side of the bristles, to effectively prevent the bristles during rotation from contacting other parts of the oral cavity, thus protecting the oral cavity.

Figure 6:
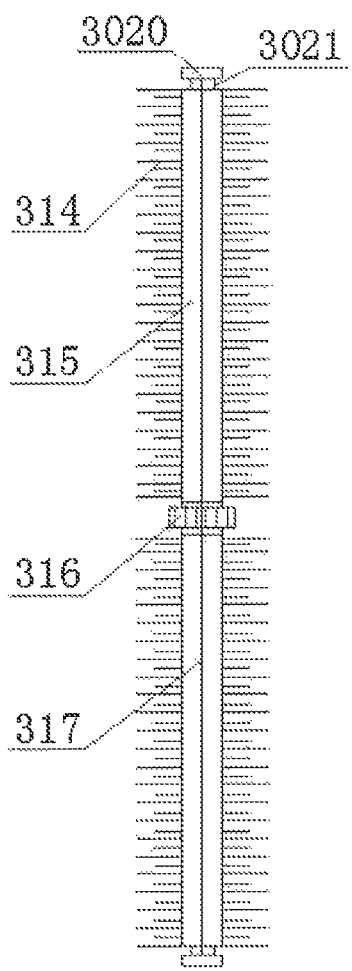
FIG. 6 is a front view of a tooth outer side brush roller (a tooth inner side brush roller) in FIG. 5.
Figure 8:
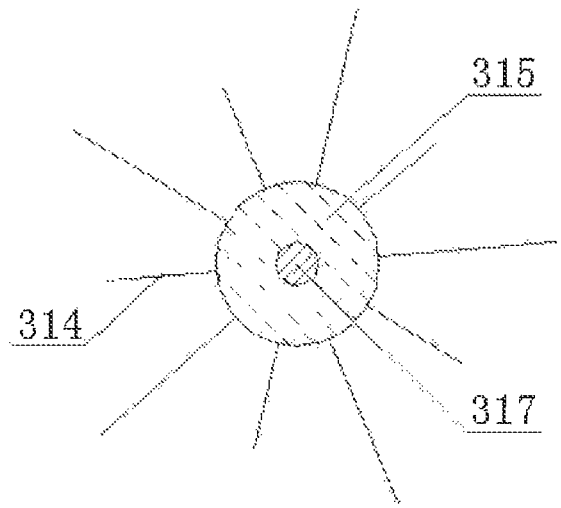
FIG. 8 is an enlarged sectional view of the tooth end surface brush roller (the tooth inner side brush roller, the tooth outer side brush roller) in FIG. 5.

As shown in FIGS. 6 and 8, the tooth outer side brush roller 302 and the tooth inner side brush roller 307 are similarly configured. Specifically, a main body part of each of the tooth outer side brush roller 302 and the tooth inner side brush roller 307 is a flexible roller bar 315, and a flexible cord 317 can be arranged in the flexible roller bar 315. The flexible roller bar 315 and the flexible cord 317 are fixedly connected to the side brush roller gear 316 coaxially, and bristles 314 are planted onto the flexible roller bar 315 at each of two sides of the side brush roller gear 316. Of course, the flexible cord 317 may not be provided in the flexible roller bar 315, and the flexible roller bar 315 is directly fixedly connected to the side brush roller gear 316 coaxially. A brush roller trailing terminal 3020 is provided at each of tip ends of the tooth outer side brush roller 302 and the tooth inner side brush roller 307, and a brush roller retaining groove 3021 is formed between the brush roller trailing terminal 3020 at the corresponding tooth outer side brush roller 302 and the flexible roller bar 315 adjacent to this brush roller trailing terminal 3020, and a brush roller retaining groove 3021 is also formed between the brush roller trailing terminal 3020 at the corresponding tooth inner side brush roller 307 and the flexible roller bar 315 adjacent to this brush roller trailing terminal 3020.

Figure 7:
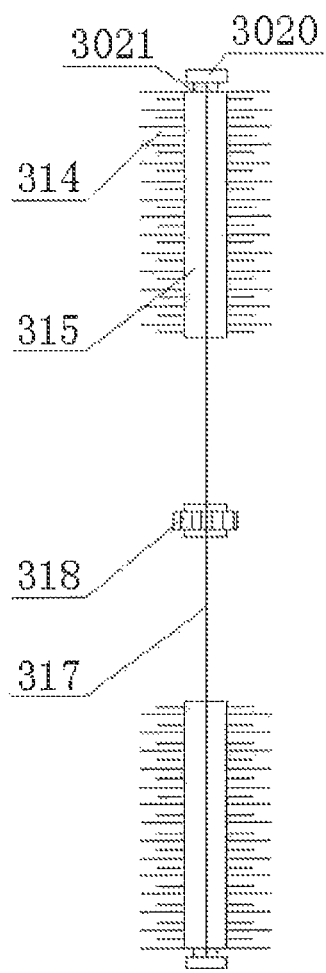
FIG. 7 is a front view of a tooth end surface brush roller in FIG. 5 (a first embodiment).

As shown in FIGS. 7 and 8, a main body part of the tooth end surface brush roller 303 is also a flexible roller bar 315, and a flexible cord 317 is provided in the flexible roller bar 315. The flexible cord 317 is fixedly connected to the end surface brush roller gear 318 coaxially, and bristles 314 are planted onto the flexible roller bar 315 at each of two sides of the end surface brush roller gear 318. A brush roller trailing terminal 3020 is provided at a tip end of the tooth end surface brush roller 303, and a brush roller retaining groove 3021 is formed between the brush roller trailing terminal 3020 at the corresponding tooth end surface brush roller 303 and the flexible roller bar 315 adjacent to this brush roller trailing terminal 3020. Compared with the tooth outer side brush roller 302 and the tooth inner side brush roller 307, a middle part of the tooth end surface brush roller 303 is not provided with the flexible roller bar 315 and the bristles 314, and is just provided with the flexible cord 317, that is, an effective length of the bristles 314 on the tooth end surface brush roller 303 is shorter.

For each of the tooth outer side brush rollers 302, the tooth end surface brush rollers 303 and the tooth inner side brush rollers 307, the flexible cord 317 therein functions as a brush roller central spindle, and is made by one or multiple strands of treads of an artificial composite material or a metal material having a high tensile strength and torsional strength, fatigue resistance and a certain deformation property, and an outer surface of the flexible cord 317 is wrapped with a round-bar-like flexible roller bar 315 having a uniform thickness or having a thick middle part and a thin trailing part, and bristles 314 are then planted onto the flexible roller bar 315. It is also possible to adopt a configuration manner in which bristles 314 are directly planted on the flexible roller bar 315. The side brush roller gear 316 and the end surface brush roller gear 318 are made of a metal material or a plastic material. The flexible roller bar 315 may be made of a rubber material or a similar flexible plastic material, and the bristle 314 is made of a plastic material, natural fibers or animal furs.

Figure 9:
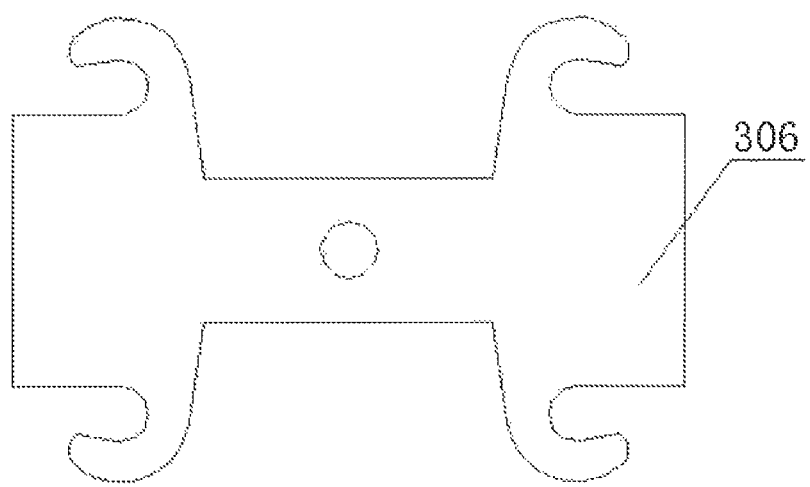
FIG. 9 is a front view of a brush roller terminal support in FIG. 5.

The tail ends of the tooth outer side brush rollers 302, the tooth inner side brush rollers 307 and the tooth end surface brush roller 303 are supported and fixed by the brush roller terminal support 306 arranged in the U-shaped brush head 3. The structure of the brush roller terminal support 306 is shown by FIG. 9, and a U-shaped positioning opening is provided at each of four corners of the brush roller terminal support 306, and a through hole is provided at a central part of the brush roller terminal support 306. Each of the tooth outer side brush rollers 302, the tooth inner side brush rollers 307 and the tooth end surface brush roller 303 is clamped to the brush roller terminal support 306 by the brush roller retaining groove 3021 at the tail end. The brush roller terminal support 306 functions to fix the tail ends of the tooth outer side brush rollers 302, the tooth inner side brush rollers 307 and the tooth end surface brush roller 303, and maintain the tooth outer side brush rollers 302, the tooth inner side brush rollers 307 and the tooth end surface brush roller 303 at proper tooth brushing positions, and also facilitate the separation and replacement of the tooth outer side brush rollers 302, the tooth inner side brush rollers 307 and the tooth end surface brush roller 303.

The tooth outer side brush rollers 302 and the tooth inner side brush rollers 307 are provided with rotating power by the side brush roller gears 316, and the tooth end surface brush roller 303 is provided with rotating power by the end surface brush roller gear 318, and the bristles 314 on the tooth end surface brush roller 303 are partially disposed in the end surface brush roller positioning groove 305 in the U-shaped base plate 310. The side brush roller gears 316 and the end surface brush roller gear 318 respectively drive the flexible cords 317, the flexible roller bars 315 and the bristles 314 fixedly connected thereto to rotate to brush teeth. Each of the tooth outer side brush rollers 302, the tooth inner side brush rollers 307, and the tooth end surface brush roller 303 is a flexible brush roller, and thus has a certain deformability, and can be better adapted to the U-shaped bar-like space, defined by the U-shaped base plate 310, the brush head sleeve 308 and the teeth, in the U-shaped brush head 3, can rotate freely to achieve tooth brushing, and has an ideal tooth brushing strength, which can effectively prevent injury to the teeth and gums, to protect the oral cavity, and be safe and reliable.

Second Embodiment

The second embodiment differs from the first embodiment in the following aspects.

The structure of the brush handle 2 is shown by FIGS. 17, 18, 19, 20 and 21. A power output mechanism of the brush handle 2 includes a central transmission shaft 8, a brush handle transmission gear 214, a rotating direction output transmission gear 216, a motor power output gear 217, a second transmission gear 327 and a fifth transmission gear 330. The central transmission shaft 8 has one end fixedly connected to the brush handle transmission gear 214 and another end fixedly connected to the second transmission gear 327 and the fifth transmission gear 330 respectively. A first transmission gear 326 and a sixth transmission gear 331 are both located at a same side of the central transmission shaft 8, and a third transmission gear 328 and a fourth transmission gear 329 are located at another same side of the central transmission shaft 8. The brush handle transmission gear 214 and the motor power output gear 217 are both spur gears, and the rotating direction output transmission gear 216 is a double-plane gear with two opposite sides being planes.

The central gearset 309 is installed inside the U-shaped brush head 3 by a gearset support housing 337 and the central gearset support 321, and has a specific configuration as shown in FIGS. 18, 19, 20 and 21. The central gearset 309 specifically includes the first transmission gear 326, the third transmission gear 328, the fourth transmission gear 329, the sixth transmission gear 331, a seventh transmission gear 332, an eighth transmission gear 333, a ninth transmission gear 334 and a tenth transmission gear 335.

The output shaft of the micro motor 218 is fixedly connected to the motor power output gear 217, and the opposite ends of the rotating direction output transmission gear 216 are respectively face gears, and are respectively engaged with the brush handle transmission gear 214 and the motor power output gear 217 in different planes to transmit power. Each of the first transmission gear 326, the third transmission gear 328, the fourth transmission gear 329 and the sixth transmission gear 331 is a gear formed by coaxially connecting a spur gear and a face gear. The face gear of each of the first transmission gear 326 and the third transmission gear 328 is engaged with the second transmission gear 327 to transmit power, and the face gear of each of the fourth transmission gear 329 and the sixth transmission gear 331 is engaged with the fifth transmission gear 330 to transmit power. The spur gear of the first transmission gear 326 is engaged with the eighth transmission gear 333 to transmit power. The spur gear of the third transmission gear 328 is engaged with the seventh transmission gear 332 to transmit power. The spur gear of the fourth transmission gear 329 is engaged with the tenth transmission gear 335 to transmit power. The spur gear of the sixth transmission gear 331 is engaged with the ninth transmission gear 334 to transmit power. Each of the seventh transmission gear 332, the eighth transmission gear 333, the ninth transmission gear 334 and the tenth transmission gear 335 is engaged with a separate side brush roller gear 316 to transmit power.

Figure 22:
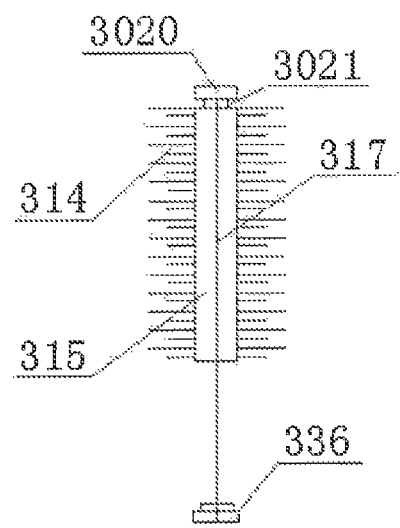
FIG. 22 is a front view of the tooth end surface brush roller in FIG. 5 (a second embodiment).

The structure of the tooth end surface brush roller 303 is shown in FIG. 22. The main body part of the tooth end surface brush roller 303 is a flexible roller bar 315, and bristles 314 are planted onto the flexible roller bar 315, and a flexible cord 317 is arranged in the flexible roller bar 315. The flexible cord 317 has one end exposed to the flexible roller bar 315, and the tip end of the flexible cord 317 exposed outside the flexible roller bar 315 is directly fixedly connected to a tooth end surface brush roller connector 336.

An outer side of the central spindle of each of the first transmission gear 326 and the third transmission gear 328 is connected to a tooth end surface brush roller connector 336 of a separate tooth end surface brush roller 303. Or, an outer side of the central spindle of each of the fourth transmission gear 329 and the sixth transmission gear 331 is connected to a tooth end surface brush roller connector 336 of a separate tooth end surface brush roller 303.

Compared with the first embodiment, the central gearset 309 in the U-shaped brush head 3 of the tooth brush according to this embodiment has a more complex structure and a larger volume.

Third Embodiment

The third embodiment differs from the second embodiment in the following.

Figure 23:
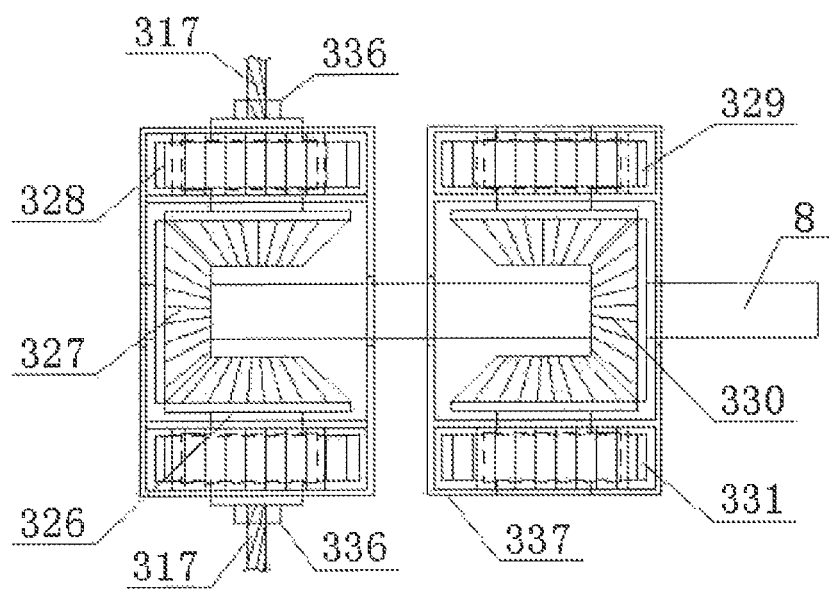
FIG. 23 is a top view of the central gearset in the U-shaped brush head (a third embodiment).
Figure 24:
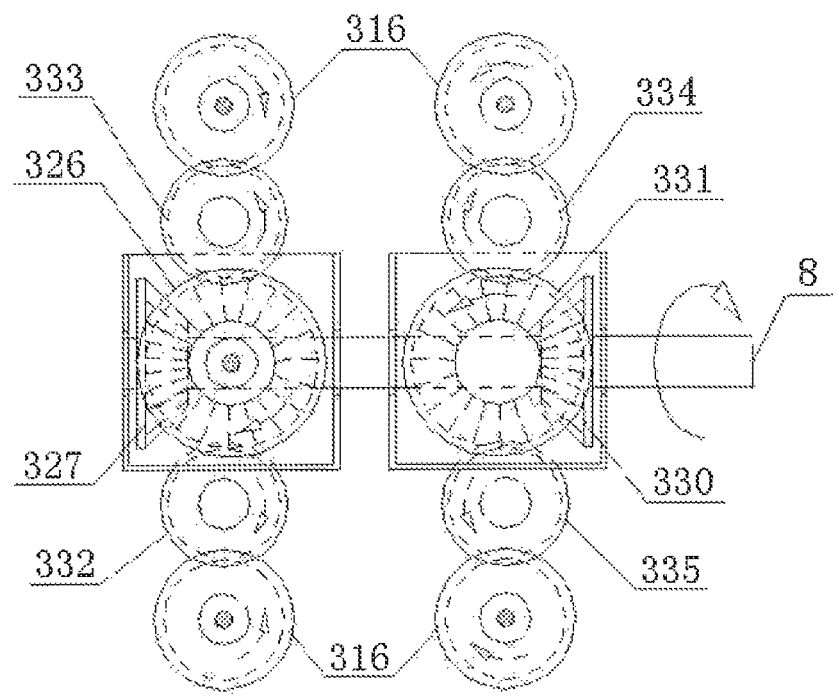
FIG. 24 is a front view of the central gearset in the U-shaped brush head (the third embodiment).
Figure 25:
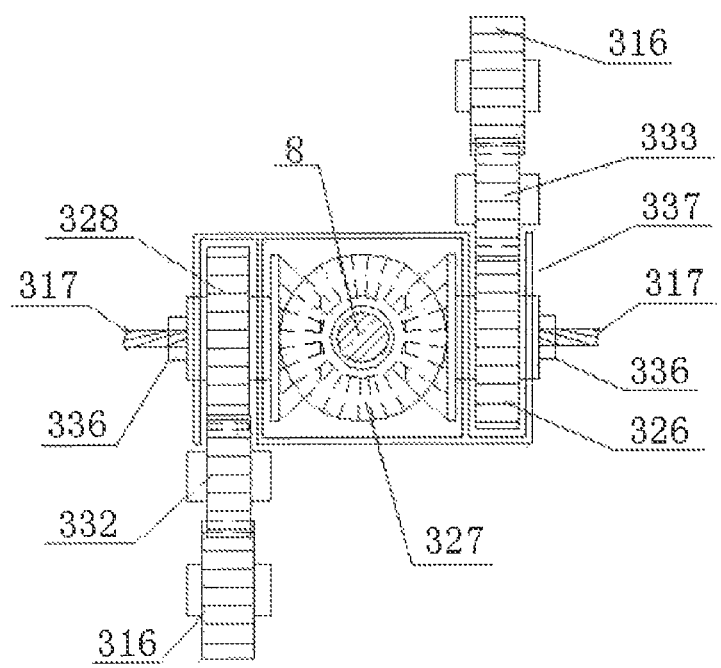
FIG. 25 is a side view of the central gearset in the U-shaped brush head (the third embodiment).

As shown in FIGS. 23, 24, and 25, each of the first transmission gear 326, the third transmission gear 328, the fourth transmission gear 329 and the sixth transmission gear 331 is formed by coaxially connecting a spur gear and a bevel gear. The second transmission gear 327 and the fifth transmission gear 330 are both bevel gears. The bevel gear of each of the first transmission gear 326 and the third transmission gear 328 is engaged with the second transmission gear 327 to transmit power. The bevel gear of each of the fourth transmission gear 329 and the sixth transmission gear 331 is engaged with the fifth transmission gear 330 to transmit power. The spur gear of the first transmission gear 326 is engaged with the eighth transmission gear 333 to transmit power. The spur gear of the third transmission gear 328 is engaged with the seventh transmission gear 332 to transmit power. The spur gear of the fourth transmission gear 329 is engaged with the tenth transmission gear 335 to transmit power. The spur gear of the sixth transmission gear 331 is engaged with the ninth transmission gear 334 to transmit power. The rest is the same as those in the second embodiment.

Compared with the second embodiment, the structure of the central gearset 309 in the U-shaped brush head 3 of the tooth brush according to this embodiment has a more complex structure and a larger volume.

Figure 26:
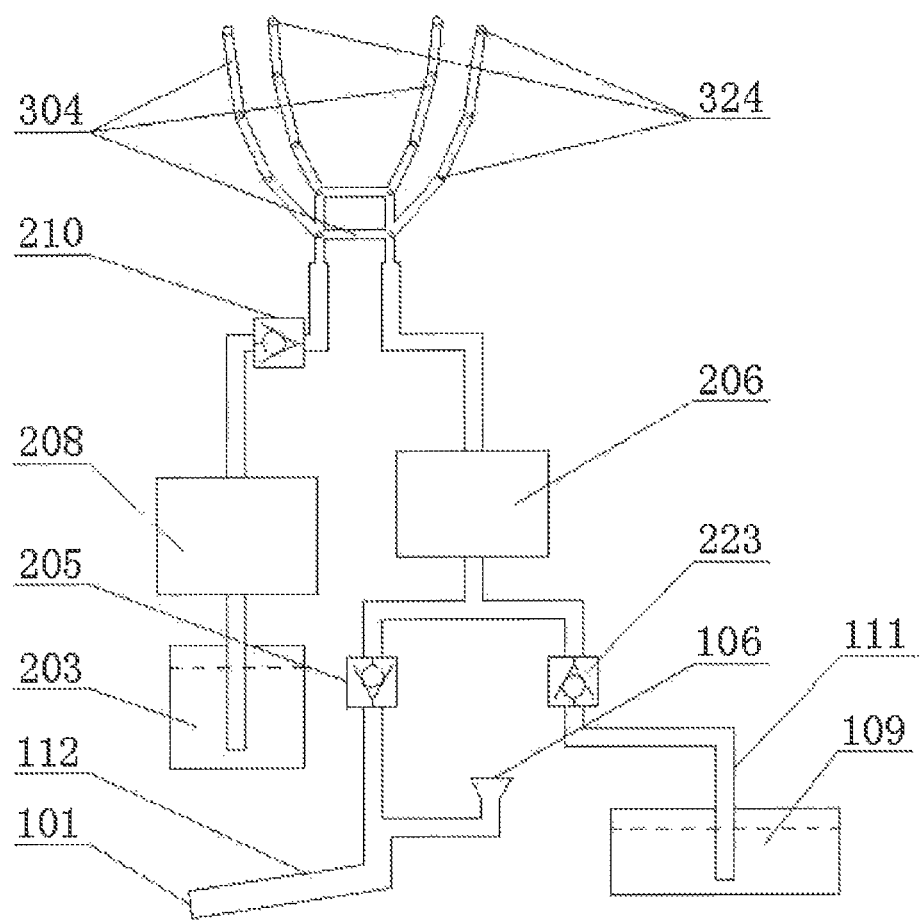
FIG. 26 is a schematic view of a full water-washing liquid system of an omnidirectional scientific toothbrush according to the present application.

The omnidirectional scientific tooth brush according to the present application includes the tooth brush according to the above first embodiment, second embodiment and third embodiment, and the tooth brush according to each of the embodiments can be provided with a water-washing liquid system shown in FIG. 26. The water-washing liquid system includes a washing liquid storage bottle 203, a first one-way valve 205, a water pumping micro pump 206, a washing liquid delivery micro pump 208, a second one-way valve 210, a third one-way valve 223, a washing liquid delivery conduit 304 and a clean water tank 109.

Specifically, as shown in FIG. 2, a clean water tank 109 is arranged inside an inner cavity of the base 1. A micro liquid level sensor 108 is arranged in the clean water tank 109. A waste water nozzle 102 and a clean water nozzle 103 are arranged at the top of the base 1. A down-flow hole 106 is provided at the center of the surface of the base 1. Multi-point metal contact 105 is provided in the brush handle groove 104 of the base 1, and a base charging socket 110 is provided at the bottom of the base 1. The clean water tank 109 is in fluid communication with the clean water nozzle 103 via a clean water conduit 111. The waste water nozzle 102 and the down-flow hole 106 are in fluid communication with the waste water conduit 112 via a tee joint. The waste water outlet 101 on the waste water conduit 112 is exposed outside the base 1. The multi-point metal contact 105 is respectively connected to the micro liquid level sensor 108 and the base charging socket 110 by wires 107.

Figure 17:
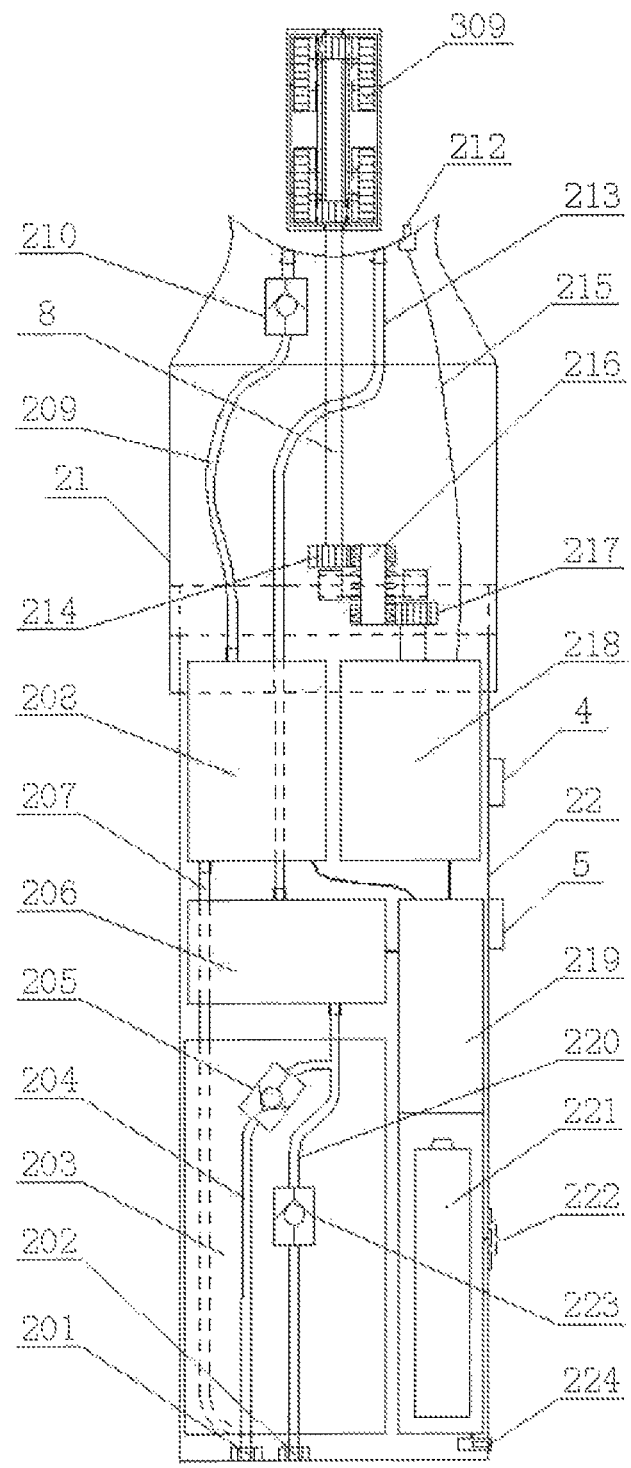
FIG. 17 is a schematic view showing the configuration of the brush handle in FIG. 1 (a second embodiment).
Figure 18:
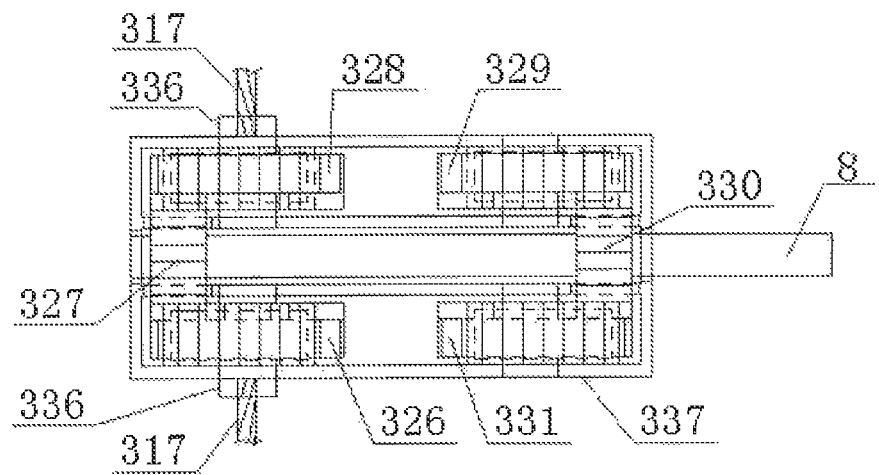
FIG. 18 is a top view of the central gearset in the U-shaped brush head (a second embodiment).
Figure 19:
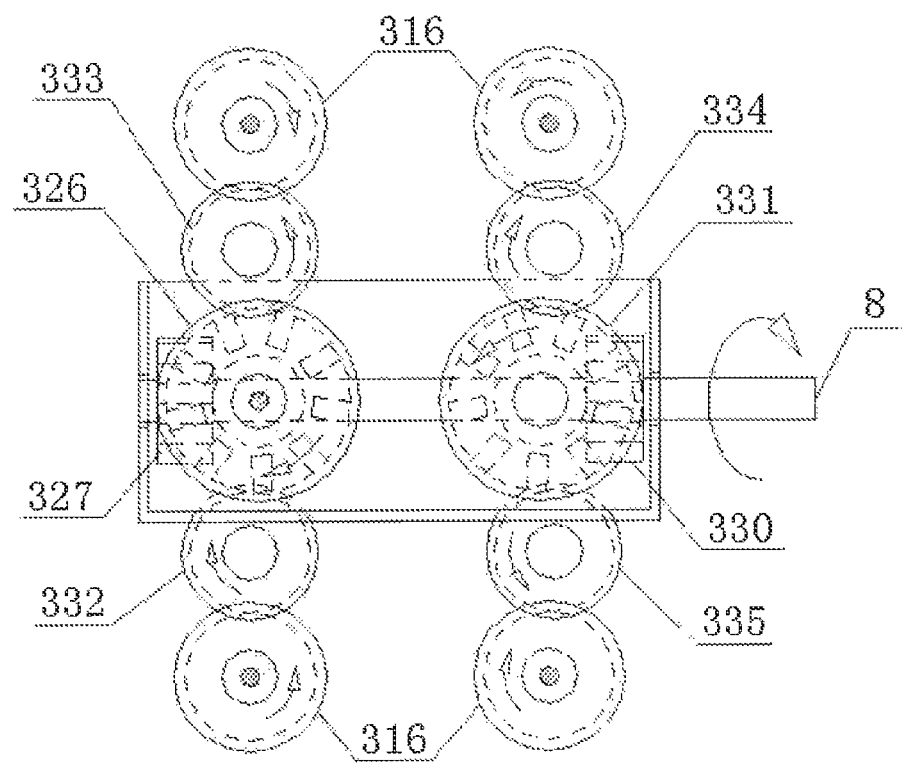
FIG. 19 is a front view of the central gearset in the U-shaped brush head (the second embodiment).
Figure 20:
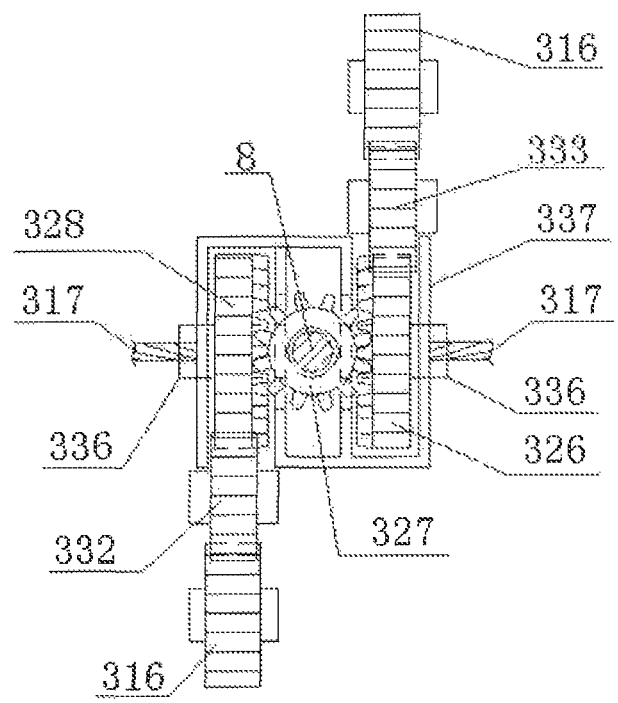
FIG. 20 is a side view of the central gearset in the U-shaped brush head (the second embodiment).

As shown in FIGS. 5 and 14, the washing liquid delivery conduit 304 is arranged in the U-shaped base plate 310 of the U-shaped brush head 3, and multiple base plate water outlets 324 are provided in the washing liquid delivery conduit 304. As shown in FIGS. 4 and 17, the washing liquid storage bottle 203, the water pumping micro pump 206 and the washing liquid delivery micro pump 208 are all arranged inside the hollow cavity of the brush handle 2. The washing liquid storage bottle 203 is in fluid communication with the washing liquid delivery micro pump 208 via a second conduit 207, and an output end of the washing liquid delivery micro pump 208 is in communication with a third conduit 209. The third conduit 209 has an outlet located at a top end of the brush handle 2, and may be provided with the second one-way valve 210. The water pumping micro pump 206 has one end connected to the first conduit 204 and the fifth conduit 220 via a tee joint and another end in communication with a fourth conduit 213. The fourth conduit 213 has an outlet located at the top end of the brush handle 2. The first conduit 204 is in communication with the lower water outlet 201. The first conduit 204 is provided with the first one-way valve 205, and the fifth conduit 220 is in communication with the lower water inlet 202, and the fifth conduit 220 is provided with the third one-way valve 223.

The water pumping micro pump 206 has one end in communication with the washing liquid delivery conduit 304 and another end in communication with the clean water conduit 111 and the waste water conduit 112 respectively. The clean water conduit 111 is provided with the third one-way valve 223, and the waste water conduit 112 is provided with the first one-way valve 205. The washing liquid delivery micro pump 208 has one end in communication with the washing liquid storage bottle 203 and another end in communication with the washing liquid delivery conduit 304. The second one-way valve 210 may be provided on a connection conduit between the washing liquid delivery micro pump 208 and the washing liquid delivery conduit 304. When clean water is required to be fed, the water pumping micro pump 206 is forwardly connected to the power supply, and when to discharge waste water, the water pumping micro pump 206 is reversely connected to the power supply.

Figure 27:
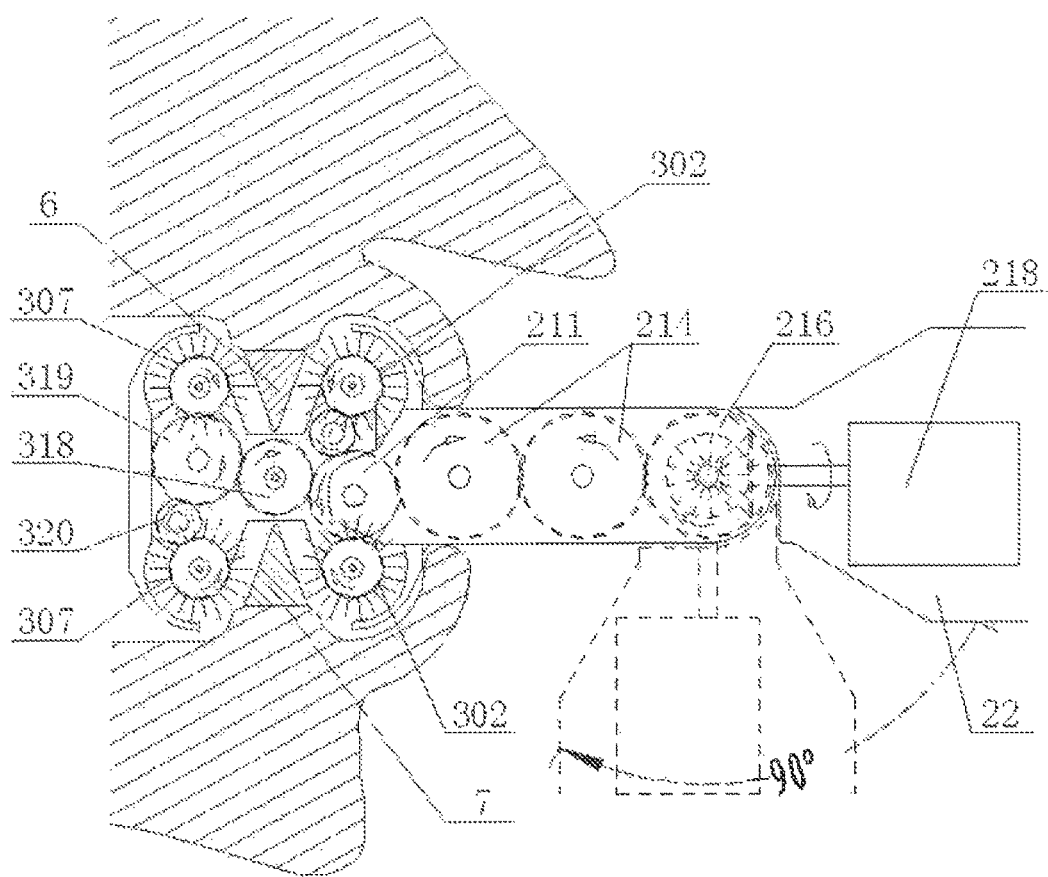
FIG. 27 is a schematic view of occlusion during teeth brushing with the omnidirectional scientific toothbrush according to the present application.

When using the above tooth brush to brush teeth, as shown in FIG. 27, upper teeth 6 in the oral cavity are sandwiched between the tooth outer side brush roller 302 and the tooth inner side brush roller 307 at the upper layer of the brush head, and lower teeth 7 are sandwiched between the tooth outer side brush roller 302 and the tooth inner side brush roller 307 at the lower layer of the brush head. After the micro motor 218 is started, the tooth outer side brush roller 302 and the tooth inner side brush roller 307 located at two sides of the same tooth are rotated in opposite directions, and the rotating directions are both from a tooth root to a tooth end. The tooth end surface brush roller 303 rotates and brushes in the direction of gaps between the end surfaces of the upper and low teeth.

Figure 21:
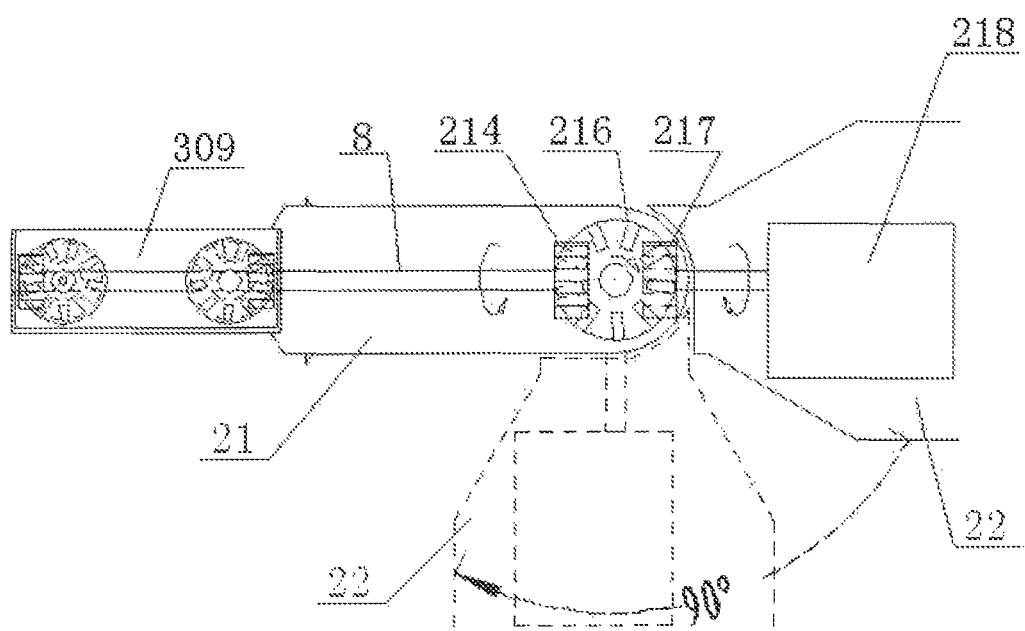
FIG. 21 is a diagram showing the principle of transmission between the U-shaped brush head and the brush handle (including the schematic diagram of the rotation direction of the brush handle).

As shown in FIGS. 1, 4, and 17, the brush handle 2 includes a brush handle rotation part 21 and a brush handle hold part 22. The brush handle rotation part 21 has one end connected to the brush head 3, and another end connected to the brush handle hold part 22, and the brush handle rotation part 21 rotates within a certain included angle range with respect to the brush handle hold part 22. Specifically, as shown in FIGS. 4 and 17, the motor power output gear 217 may rotate along the axis of the rotating direction output transmission gear 216 engaged with it, for example, may rotate by 90 degrees, as shown in FIGS. 16 and 21. That is, an angle between the U-shaped brush head 3 embedded in the brush handle head and the brush handle hold part 22 can be adjusted, and the rotatable brush handle head enables the user to adjust an included angle between the brush handle hold part 22 and the brush head of the tooth brush according to suitable posture when brushing teeth, thus improving the convenience and comfort of the tooth brush user to the utmost.

Figure 28:
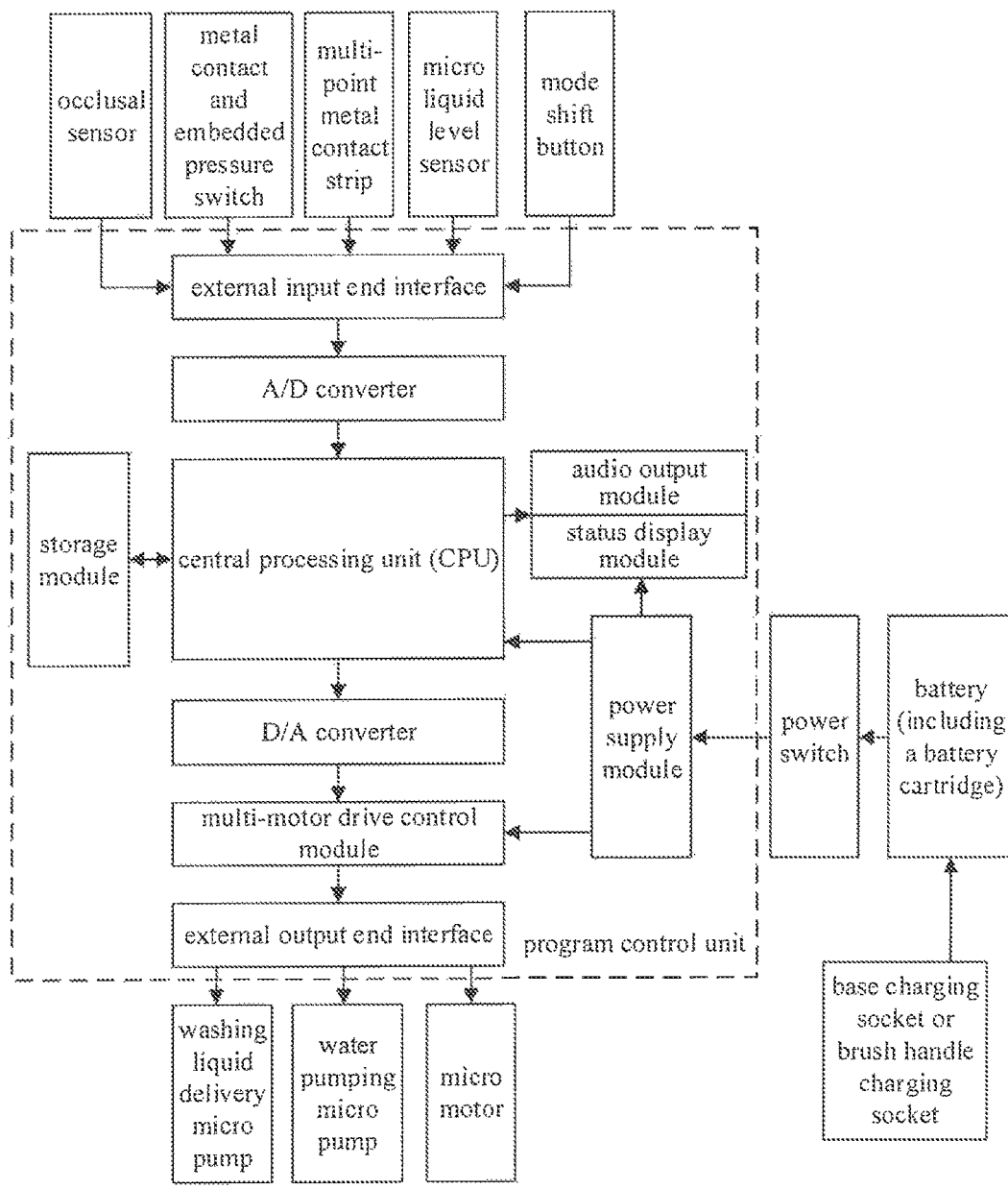
FIG. 28 is a schematic view showing the functional module components of a program control unit in an omnidirectional scientific toothbrush according to the present application and their connections with external units.

In order to realize automatic tooth brushing and meet individualized brushing needs of different users, a micro liquid level sensor 108 is provided in the clean water tank 109 on the base 1, and the occlusal sensor 311 is installed on each of the upper surface and the lower surface of the U-shaped base plate 310 in the U-shaped brush head 3. As shown in FIGS. 4 and 17, a program control unit 219 and an audio output module and a status display module are provided in the inner cavity of the brush handle 2. A metal contact and embedded pressure switch 212 at the top of the brush handle 2 is electrically connected to the program control unit 219 via a wire 215. As shown in FIG. 28, the occlusal sensor 311, the metal contact and embedded pressure switch 212, the multi-point metal contact 222, the micro liquid level sensor 108 and the mode shift button 5 as information input ends are respectively connected to the program control unit 219, and the washing liquid delivery micro pump 208, the water pumping micro pump 206, the micro motor 218 as information output ends are respectively connected to the program control unit 219. The base charging socket 110 is connected in parallel with the brush handle charging socket 224 and is then connected to the battery 221, and a power switch 4 is connected between the battery 221 and the program control unit 219. The audio output module and the status display module are respectively electrically connected to the program control unit 219.

When the brush handle 2 is inserted and placed into the brush handle groove 104 on the base 1, the clean water nozzle 103 of the base 1 is in fluid communication with the lower water inlet 202 on the brush handle 2, so as to provide clean water for brushing teeth and washing. The waste water nozzle 102 of the base 1 is in fluid communication with the lower water outlet 201 of the brush handle to discharge the waste water after washing or cleaning and the waste water scattered on the surface of the base cover plate 11 and collected to the down-flow hole 106 at the center of the surface of the base 1 out of the waste water outlet 101. The multi-point metal contact strip 222 of the brush handle 2 comes into contact and butt-jointed with the multi-point metal contact 105 of the base 1 to allow the both to control the circuit to be electrically connected. Moreover, when two contact strips in the multi-point metal contact strip 222 are connected, it is determined that the tooth brush can perform tooth brushing in a full automatic mode, and simultaneously, the micro liquid level sensor 108 is in communication with the program control unit 219 to determine whether to remind the user to feed clean water for the clean water tank 109, and also when the base charging socket 110 is in communication with the brush handle charging socket 224, it is determined that the base charging socket 110 can supply power to the brush handle 2.

Figure 29:
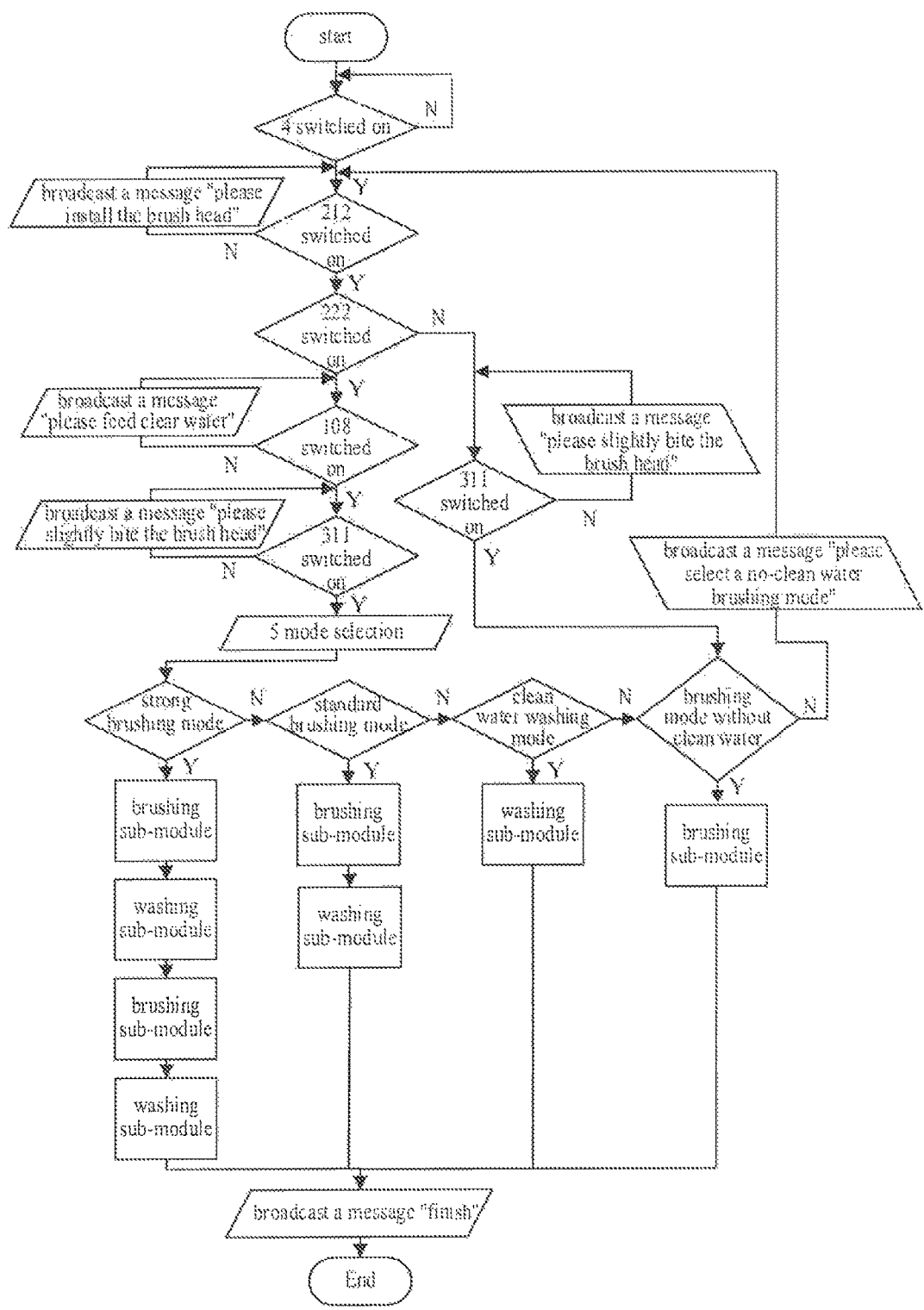
FIG. 29 is a diagram showing the principle of automatic brushing control of an omnidirectional scientific toothbrush according to the present application.

The program control circuit system of the above full automatic toothbrush takes the program control unit 219 in the brush handle 2 as a core, and the program control unit 219 is configured to control the brushing process. The program control unit 219 receives information from input ends of the occlusal sensor 311, the micro liquid level sensor 108, the multi-point metal contact strip 222, the metal contact and embedded pressure switch 212 and the mode shift button 5 and may realize various different brushing modes, for example, strong brushing mode, standard brushing mode, clean water washing mode, and brushing mode without clean water by timely controlling the operation of output devices such as the washing liquid delivery micro pump 208, the water pumping micro pump 206, the micro motor 218, the audio output module such as a loudspeaker, and the status display module such as the display screen, as shown in FIG. 29.

The strong brushing mode includes performing a brushing sub-module first, and then performing a washing sub-module, and then finishing after one cycle in the listed sequence. The standard brushing mode includes performing the brushing sub-module first, and then performing the washing sub-module, and then finishing. The clean water washing mode includes simply performing the washing sub-module and then finishing. The brushing mode without clean water includes simply performing the brushing sub-module and then finishing.

Figure 30:
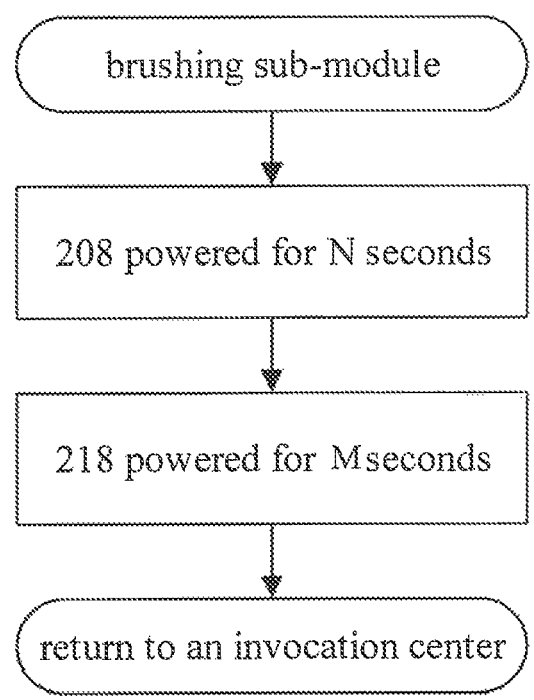
FIG. 30 is a diagram showing the working principle of a brushing sub-module in FIG. 29.
Figure 31:
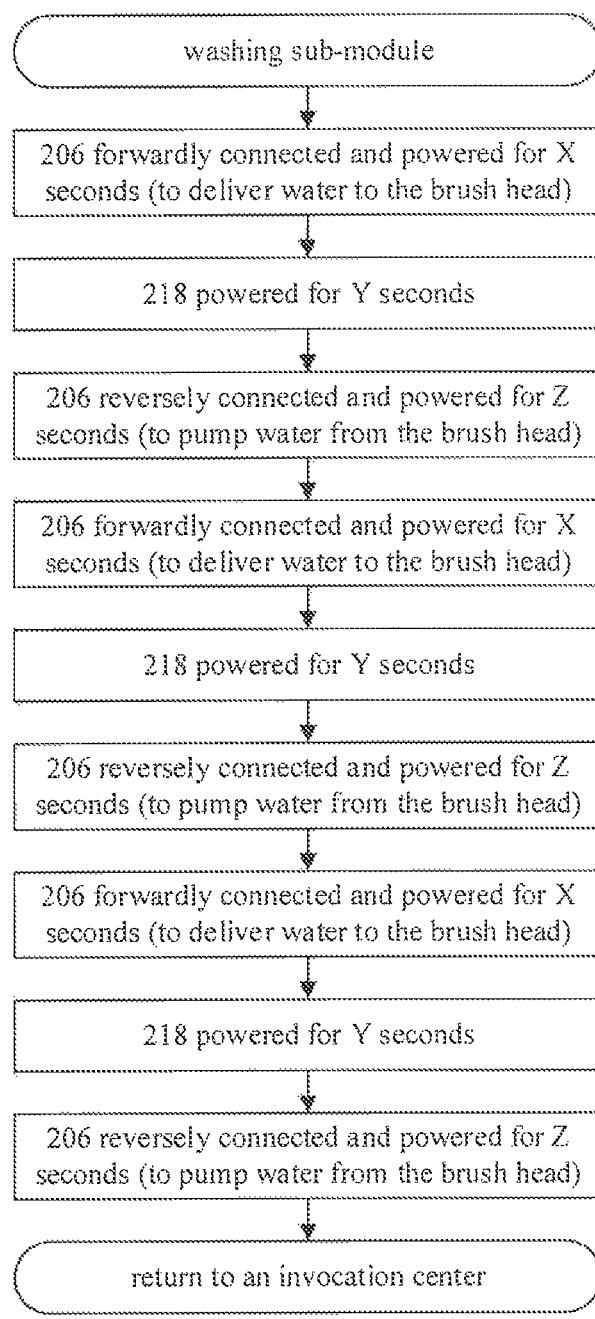
FIG. 31 is a diagram showing the working principle of a washing sub-module in FIG. 29.

The working process of the brushing sub-module is shown in FIG. 30, the washing liquid delivery micro pump 208 is powered for a certain time first, and then the micro motor 218 is powered, to drive the bristles 314 to rotationally brush for a certain time, and then the brushing process finishes. The working process of the washing sub-module is shown in FIG. 31, the water pumping micro pump 206 is forwardly connected and powered for a certain time, to deliver water into the U-shaped brush head 3, and then the micro motor 218 is powered, to allow the bristles 314 to rotationally brush for a certain time, and next, the water pumping micro pump 206 is reversely connected and powered for a certain time, to pump water from the U-shaped brush head 3. The cycle is performed in the listed sequence for two times as generally set, to finish the washing process.

The brush handle 2 of the automatic scientific brush mainly functions to provide a mechanical power, provide the washing liquid, feed clean water, discharge waste water for the U-shaped brush head 3 and connect the occlusal sensor 311 on the U-shaped brush head 3, as well as to perform test to water/electric connection for the base 1. The U-shaped brush head 3 is connected to the brush handle 2 by being embedded into the brush handle 2, and during connection, the contact gears of the brush head 3 and the brush handle 2 are engaged and abutted, to allow the mechanical transmission systems of the both to be connected. The micro motor 218 outputs power to the central gearset 309, and the tooth outer side brush roller 302, the tooth inner side brush roller 307 and the tooth end surface brush roller 303 in the U-shaped brush head 3 are driven by the central gearset 309 to rotate to brush teeth. The washing liquid delivery conduit 304 and the base plate water outlet 324 arranged in the U-shaped brush head 3 can input the washing liquid and clean water and discharge waste water for the brushing process of the U-shaped brush head 3. The occlusal sensor 311 arranged on the U-shaped brush head 3 can determine the proper time for starting, interrupting and stopping the tooth brushing, thereby may realize the integrated intelligent control for inputting tooth washing liquid, tooth brushing, water feeding, rinsing and waste water discharging, thus, the full-scale washing task for the teeth can be performed fully automatically one time in about 20 to 40 seconds, which greatly improves the cleaning quality and efficiency of the tooth brushing, and significantly reduces the time and energy consumption in the tooth brushing.

Figure 3:
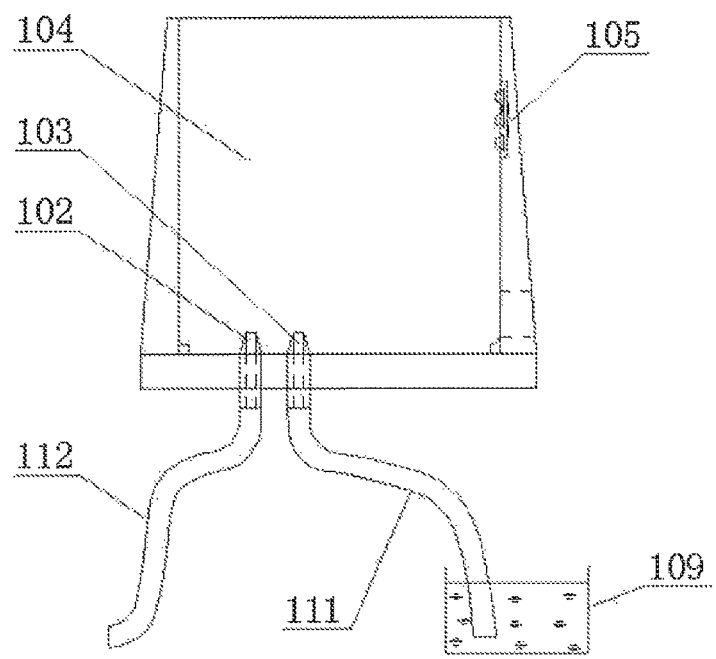
FIG. 3 is a schematic view showing the structure of the base in FIG. 1 (a second embodiment).

It is to be noted that, for facilitating carrying the toothbrush, a simple type base 1 shown in FIG. 3 may be adopted. The waste water nozzle 102 is in fluid communication with the waste water conduit 112, the clean water nozzle 103 is in communication with the clean water conduit 111, and the multi-point metal contact 105 has a part preset to be closed. Compared with the structure of the base shown in FIG. 2, the micro liquid level sensor 108 and the base charging socket 110 are removed, and the large volume clean water tank 109, and the water tank cover, i.e., the base cover plate 11 are replaced by other water containers common in life, such as a water cup, a bowl or the like, and a short circuit connection of a part of the multi-point metal contact 105 is additionally provided. In this case, fully automatic tooth brushing functions are still reserved, it is just a little bit inconvenient in using the toothbrush, however, the cost is reduced, and the overall volume of the toothbrush is reduced, which is more suitable for using when going out of home or outdoors.

In summary, the brush head of the scientific toothbrush according to the present application has a U shape, which confirms to the human engineering better, and can be made into different types with different shapes and sizes according to different sizes of mouth types, and different shapes and widths of teeth, so as to be suitable for different people to perform omnidirectional accurate and scientific tooth brushing, thus maximally improving the quality and efficiency of tooth brushing. In addition, the scientific toothbrush according to the present application is different from any toothbrushes with a small brush surface common in the market, and the bristles on all of the brush rollers, controlled by the motor, can brush all of the teeth in the mouth in scientific directions, that is always from roots of the teeth to tips of the teeth and along gaps of the teeth in scrubbing the occlusal surfaces of the teeth without requiring the user to manually control the toothbrush. Moreover, the U-shaped brush head 3 of the toothbrush and the brush roller therein can be detached and replaced, thus, multiple users can share the brush handle 2 and the base 1, such that the daily use cost of the toothbrush can be significantly reduced, which facilitates resource sharing and utilization, and is therefore more environment friendly and cost efficient.

Only preferred embodiments of the present application are described hereinbefore, and are not intended to limit the present application. It should be noted that, any modifications, equivalent substitutions and improvements made within the spirit and principle of the present application should be covered in the scope of protection of the present application.

The invention claimed is:

1. An omnidirectional scientific toothbrush, comprising:
a brush handle, and
a brush head, Wherein
the brush head has a U-shaped structure, a central gearset, and tooth outer side brush rollers, tooth inner side brush rollers and tooth end surface brush rollers which are driven by the central gearset are installed in an inner cavity of the brush head;
the tooth outer side brush rollers and the tooth inner side brush rollers are both arranged in an upper row and a lower row which are opposite according to a tooth layout in an oral cavity of human body, and main body parts of each tooth outer side brush roller and each tooth inner side brush roller are both flexible roller bars, a side brush roller gear is fixedly connected to each flexible roller bar, and bristles are planted onto the flexible roller bars at two sides of the side brush roller gear, the tooth end surface brush roller is located in a space defined by the tooth outer side brush rollers and the tooth inner side brush rollers;
a main body part of the tooth end surface brush roller is a flexible roller bar, a flexible cord is provided in the flexible roller bar and bristles are planted onto the flexible roller bar; and
a power output mechanism driven by a micro motor is arranged in the brush handle, the power output mechanism drives the central gearset to move to allow the tooth outer side brush roller and the tooth inner side brush roller located at two sides of the same tooth to rotate in opposite directions and to have rotating directions which are both from a tooth root to a tooth end, and rotation of the tooth end surface brush roller allows the tooth end surface brush roller to simultaneously brush occlusal surfaces of upper and lower teeth in the oral cavity.

2. The omnidirectional scientific toothbrush according to claim 1, wherein:
the central gearset comprises a primary transmission gear, a lower secondary transmission gear and an upper secondary transmission gear, the tooth outer side brush rollers and the tooth inner side brush rollers are fixedly connected to the side brush roller gears respectively, the tooth end surface brush roller is fixedly connected to the end surface brush roller gear; and
the end surface brush roller gear is engaged with the primary transmission gear to transmit power, the primary transmission gear is engaged with the lower secondary transmission gear to transmit power, and each of the primary transmission gear, the lower secondary transmission gear and the upper secondary transmission gear is engaged with a separate side brush roller gear to transmit power.

3. The omnidirectional scientific toothbrush according to claim 2, wherein the power output mechanism of the brush handle comprises a power output gear, a brush handle transmission gear, a rotating direction output transmission gear and a motor power output gear;
an output shaft of the micro motor is fixedly connected to the motor power output gear, and the rotating direction output transmission gear is formed by a bevel gear and a spur gear connected coaxially, the motor power output gear is a bevel gear and is engaged with the bevel gear of the rotating direction output transmission gear to transmit power, the brush handle transmission gear is engaged with the power output gear and the spur gear of the rotating direction output transmission gear respectively, the power output gear is engaged with the end surface brush roller gear and the upper secondary transmission gear respectively to transmit power, and the primary transmission gear, the lower secondary transmission gear, the upper secondary transmission gear and the power output gear are respectively engaged with a separate side brush roller gear to transmit power.

4. The omnidirectional scientific toothbrush according to claim 2, wherein the flexible cord in the flexible roller bar is fixedly connected to the end surface brush roller gear, and bristles are planted onto the flexible roller bar at each of two sides of the end surface brush roller gear.

5. The omnidirectional scientific toothbrush according to claim 1, wherein the central gearset comprises a first transmission gear, a third transmission gear, a fourth transmission gear, a sixth transmission gear, a seventh transmission gear, an eighth transmission gear, a ninth transmission gear and a tenth transmission gear, and the tooth outer side brush rollers and the tooth inner side brush rollers are fixedly connected to side brush roller gears respectively;
each of the first transmission gear, the third transmission gear, the fourth transmission gear and the sixth transmission gear is formed by coaxially connecting a spur gear and a face gear, the spur gear of the first transmission gear is engaged with the eighth transmission gear to transmit power, the spur gear of the third transmission gear is engaged with the seventh transmission gear to transmit power, the spur gear of the fourth transmission gear is engaged with the tenth transmission gear to transmit power, and the spur gear of the sixth transmission gear is engaged with the ninth transmission gear to transmit power; and
each of the seventh transmission gear, the eighth transmission gear, the ninth transmission gear and the tenth transmission gear is engaged with a separate side brush roller gear to transmit power, and outer sides of the first transmission gear and the third transmission gear are respectively connected to the tooth end surface brush roller, or outer sides of the fourth transmission gear and the sixth transmission gear are respectively connected to the tooth end surface brush roller.

6. The omnidirectional scientific toothbrush according to claim 5, wherein the power output mechanism of the brush handle comprises a central transmission shaft, a brush handle transmission gear, a rotating direction output transmission gear, a motor power output gear, a second transmission gear and a fifth transmission gear, wherein:
    the central transmission shaft has one end fixedly connected to the brush handle transmission gear and another end fixedly connected to the second transmission gear and the fifth transmission gear respectively;
    the first transmission gear and the sixth transmission gear are located on a same side of the central transmission shaft, and the third transmission gear and the fourth transmission gear are located on another same side of the central transmission shaft;
    the output shaft of the micro motor is fixedly connected to the motor power output gear, and opposite ends of the rotating direction output transmission gear are face gears respectively and the face gears are respectively engaged with the brush handle transmission gear and the motor power output gear in different planes to transmit power; and
    the face gears of the first transmission gear and the third transmission gear are respectively engaged with the second transmission gear to transmit power, and the face gears of the fourth transmission gear and the sixth transmission gear are respectively engaged with the fifth transmission gear to transmit power.

7. The omnidirectional scientific toothbrush according to claim 5, wherein a tip end of the flexible cord in the flexible roller bar is fixedly connected to a tooth end surface brush roller connector.

8. The omnidirectional scientific toothbrush according to claim 1, wherein the central gearset comprises a first transmission gear, a third transmission gear, a fourth transmission gear, a sixth transmission gear, a seventh transmission gear, an eighth transmission gear, a ninth transmission gear and a tenth transmission gear, and the tooth outer side brush rollers and the tooth inner side brush rollers are fixedly connected to side brush roller gears respectively;
    each of the first transmission gear, the third transmission gear, the fourth transmission gear and the sixth transmission gear is formed by coaxially connecting a spur gear and a bevel gear, the spur gear of the first transmission gear is engaged with the eighth transmission gear to transmit power, the spur gear of the third transmission gear is engaged with the seventh transmission gear to transmit power, the spur gear of the fourth transmission gear is engaged with the tenth transmission gear to transmit power, and the spur gear of the sixth transmission gear is engaged with the ninth transmission gear to transmit power; and
    each of the seventh transmission gear, the eighth transmission gear, the ninth transmission gear and the tenth transmission gear is engaged with a separate side brush roller gear to transmit power, and outer sides of the first transmission gear and the third transmission gear are respectively connected to the tooth end surface brush roller, or outer sides of the fourth transmission gear and the sixth transmission gear are respectively connected to the tooth end surface brush roller.

9. The omnidirectional scientific toothbrush according to claim 8, wherein the power output mechanism of the brush handle comprises a central transmission shaft, a brush handle transmission gear, a rotating direction output transmission gear, a motor power output gear, a second transmission gear and a fifth transmission gear, the central transmission shaft has one end fixedly connected to the brush handle transmission gear and another end fixedly connected to each of the second transmission gear and the fifth transmission gear;
    the first transmission gear and the sixth transmission gear are located on a same side of the central transmission shaft, and the third transmission gear and the fourth transmission gear are located on another same side of the central transmission shaft;
    the output shaft of the micro motor is fixedly connected to the motor power output gear, and opposite ends of the rotating direction output transmission gear are face gears respectively and the face gears are respectively engaged with the brush handle transmission gear and the motor power output gear in different planes to transmit power; and
    each of the second transmission gear and the fifth transmission gear is a bevel gear, and the bevel gears of the first transmission gear and the third transmission gear are respectively engaged with the second transmission gear to transmit power, and the bevel gears of the fourth transmission gear and the sixth transmission gear are respectively engaged with the fifth transmission gear to transmit power.

10. The omnidirectional scientific toothbrush according to claim 1, further comprising a U-shaped base plate, wherein an overall structure of the U-shaped base plate is U-shaped, and a central gearset arranging groove is provided at a central part of the U-shaped base plate, and each of two branches of the U-shaped base plate is provided with an end surface brush roller positioning groove from a middle part to a tip end of the branch of the U-shaped base plate.

11. The omnidirectional scientific toothbrush according to claim 10, further comprising a U-shaped brush head sleeve made of a flexible plastic material, wherein the brush head sleeve is supported by the U-shaped base plate and surrounds an outer edge of the U-shaped base plate, and the brush head sleeve surrounds an outer side and, an upper side or a lower side of the bristles.

12. The omnidirectional scientific toothbrush according to claim 10, further comprising a water-washing liquid system, wherein the water-washing liquid system comprises a washing liquid storage bottle, a first one-way valve, a water pumping micro pump, a washing liquid delivery micro pump, a third one-way valve and a washing liquid delivery conduit;
    the washing liquid delivery conduit is installed in the brush head, the washing liquid delivery conduit is provided with a base plate water outlet, and the water pumping micro pump has one end in communication with the washing liquid delivery conduit and another end in communication with a clean water conduit and a waste water conduit, the clean water conduit is provided with the third one-way valve, and the waste water conduit is provided with the first one-way valve, the washing liquid delivery micro pump has one end in communication with the washing liquid storage bottle and another end in communication with the washing liquid delivery conduit.

13. The omnidirectional scientific toothbrush according to claim 12, further comprising a clean water tank, wherein a micro liquid level sensor is provided in the clean water tank, the brush handle is provided with a program control unit, an occlusal sensor is mounted on each of an upper surface and a lower surface of the U-shaped base plate in the brush head, the occlusal sensor and the micro liquid level sensor are respectively electrically connected to an input end of the program control unit, and each of the washing liquid delivery micro pump, the water pumping micro pump, the micro motor is electrically connected to an output end of the program control unit.

14. The omnidirectional scientific toothbrush according to claim 13, wherein the program control unit is configured to control brushing process and performs four tooth brushing modes, which comprise: a strong brushing mode, a standard brushing mode, a clean water washing mode and a brushing mode without clean water, wherein:

the strong brushing mode comprises performing a brushing sub-module first, and then performing a washing sub-module, and then cycling in the listed sequence till finishing the tooth brushing;

the standard brushing mode comprises performing the brushing sub-module first, and then performing the washing sub-module, and then finishing;

the clean water washing mode comprises only performing the washing sub-module and then finishing; and the brushing mode without clean water comprises only performing the brushing sub-module and then finishing; wherein, the brushing sub-module comprises powering the washing liquid micro pump for a certain time, and then powering the micro motor, to drive the bristles to rotationally brush for a certain time, and then finishing the brushing process; and the washing sub-module comprises forwardly connecting and powering the water pumping micro pump for a certain time, to deliver water to the brush head, and then powering the micro motor, to drive the bristles to rotationally brush for a certain time, and next, reversely connecting and powering the water pumping micro pump for a certain time, to pump water from the brush head.

15. The omnidirectional scientific toothbrush according to claim 1, further comprising a brush roller terminal support, wherein a U-shaped positioning opening is provided at each of four corners of the brush roller terminal support, and each of the tooth outer side brush rollers, the tooth inner side brush rollers and the tooth end surface brush roller is retained, by a brush roller retaining groove at respective tail end, to the brush roller terminal support.

16. The omnidirectional scientific toothbrush according to claim 1, wherein the brush handle includes a brush handle rotation part and a brush handle hold part, the brush handle rotation part has one end connected to the brush head and another end connected to the brush handle hold part, and the brush handle rotation part rotates within a certain range of angle with respect to the brush handle hold part.

* * * * *